(12) United States Patent
White et al.

(10) Patent No.: US 7,829,342 B2
(45) Date of Patent: Nov. 9, 2010

(54) SELECTIVE ALIPHATIC C-H OXIDATION

(75) Inventors: M. Christina White, Champaign, IL (US); Mark S. Chen, Champaign, IL (US)

(73) Assignee: The Board of Trustees of the Universiy of Illinois, Urbana, IL (US)

( * ) Notice: Subject to any disclaimer, the term of this patent is extended or adjusted under 35 U.S.C. 154(b) by 32 days.

(21) Appl. No.: 12/245,086

(22) Filed: Oct. 3, 2008

(65) Prior Publication Data

US 2009/0221083 A1  Sep. 3, 2009

Related U.S. Application Data

(60) Provisional application No. 60/977,271, filed on Oct. 3, 2007.

(51) Int. Cl.
  *G01N 33/00* (2006.01)
(52) U.S. Cl. .................. 436/127; 502/100; 502/167; 546/2
(58) Field of Classification Search .......... 436/127; 502/100, 167; 546/2
See application file for complete search history.

(56) References Cited

PUBLICATIONS

Costas et al. "Ligand Topology Tuning of Non-Heme Iron-Catalyzed Hydrocarbon Oxidations". 2003. Journal of Inorganic Biochemistry. vol. 96. p. 120.*

Chen, et al., "Evidence for the participation of a high-valent iron-oxo species in stereospecific alkane hydroxylation by a non-heme", "Chem. Commun.", 1999, pp. 1375-1376.

Fujita, et al., "In situ Formation of Peracetic Acid in Iron-Catalyzed Epoxidations by Hydrogen Peroxide in the Presence of Acetic Acid", "Adv. Synth. Catal.", 2004, pp. 190-194, vol. 346.

Hamada, et al., "Enzymatic Oxidation of 1,4- and 1,8-Cineole using Plant Cultured Cells of *Catharanthus roseus*", "Letters in Organic Chemistry", 2004, pp. 171-172, vol. 1, No. 2.

Hu, et al., "Methane Monooxygenase Models", "Biomimetic Oxidations Catalyzed by Transition Metal Complexes", 2000, pp. 269-307.

Liu, et al., "Stereochemistry of microbiological hydroxylations of 1,4-cineole", "Journal of Organic Chemistry", 1988, pp. 5700-5704, vol. 53, No. 24.

Okuno, et al., "u-Oxo bridged diiron (III) complexes and hydrogen peroxide: oxygenation and catalase-like activities", "J. Chem. Soc, Dalton Trans.", 1997, pp. 3547-3551.

(Continued)

*Primary Examiner*—Yelena G Gakh
*Assistant Examiner*—David Weisz
(74) *Attorney, Agent, or Firm*—Blanchard & Associates

(57) ABSTRACT

A composition including a complex of a metal, a tetradentate ligand, at least one ancillary ligand, and a counterion may be used for selective $sp^3$ C—H bond oxidation. The tetradentate ligand may include a N-heterocyclic-N,N'-bis(pyridyl)-ethane-1,2-diamine group or a N,N'-bis(heterocyclic)-N,N'-bis(pyridyl)-ethane-1,2-diamine group. The composition can be used in combination with $H_2O_2$ to effect highly selective oxidations of unactivated $sp^3$ C—H bonds over a broad range of substrates. The site of oxidation can be predicted, based on the electronic and/or steric environment of the C—H bond. In addition, the oxidation reaction does not require the presence of directing groups in the substrate.

19 Claims, 5 Drawing Sheets

OTHER PUBLICATIONS

Parshikov, et al., "Transformation of artemisinin by *Cunninghamella elegans*", "Applied Microbiology and Biotechnology", 2004, pp. 782-786, vol. 64.

Schmidt, et al., "Oxidative metabolic profiling of xenobiotics by human P450s expressed in tobacco cell suspension cultures", "Biochemical Society Transactions", 2006, pp. 1241-1245, vol. 34, No. 6.

Urlacher, et al., "Microbial P450 enzymes in biotechnology", "Appl Microbiol Biotechnol", 2004, pp. 317-325, vol. 64.

Van Beilen, et al., "Practical issues in the application of oxygenases", "Trends in Biotechnology", Apr. 2003, pp. 170-177, vol. 21, No. 4.

White, et al., "A Synthetically Useful, Self-Assembling MMO Mimic System for Catalytic Alkene Epoxidation with Aqueous H2O2", "Journal of the American Chemical Society", Jun. 29, 2001, pp. 7194-7195, vol. 123.

Zhan, et al., "Microbial transformations of artemisinin by *Cunninghamella echinulata* and *Aspergillus niger*", "Tetrahedron Letters", 2002, pp. 4519-4521, vol. 43.

* cited by examiner

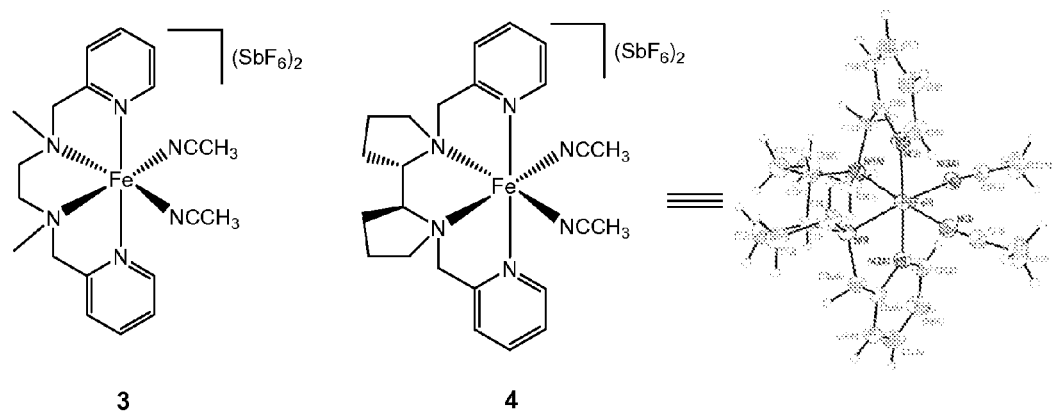
FIG. 1
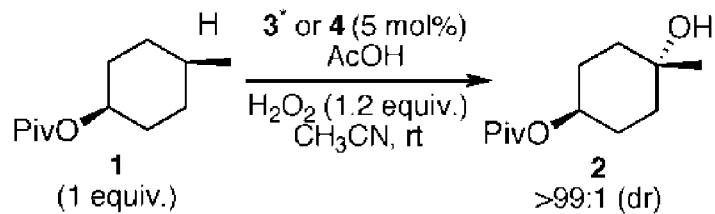
| Entry | Complex | AcOH (equiv.) | Yield (%) | Conv.† (%) | Select.‡ (%) |
|---|---|---|---|---|---|
| 1 | 3* | 0 | 7 | 12 | 56 |
| 2 | 4 | 0 | 14 | 15 | 92 |
| 3 | 3* | 0.5 | 26 | 41 | 62 |
| 4 | 4 | 0.5 | 38 | 42 | 90 |
| 5§ | 4 | 0.5 | 51 | - | - |
*[Fe(mep)(CH$_3$CN)$_2$](SbF$_6$)$_2$ (3). †Conversion of starting material. ‡Selectivity for desired product (yield/conversion). §Iterative addition protocol (isolated yield).
mep = 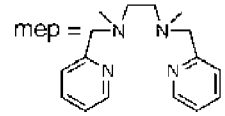
FIG. 2

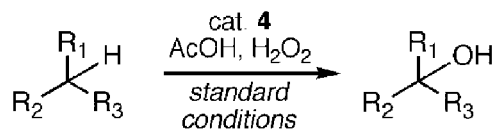

| Entry | Substrate | Major Product | | Isolated %Yield* (rsm)† | [Remote: Proximal]‡ |
|---|---|---|---|---|---|
| 1 | remote proximal | | 15, X = H | 48§(29) | 1:1 |
| 2 | H↙ H↙ β  X  α | HO H  X | 16, X = OAc | 43 (35) | 5:1 |
| 3 | | | 17, X = Br | 39 (32) | 9:1 |
| 4 | | | 18, X = F | 43 (20) | 6:1 |
| 5 | H H  X  α | HO H  X | 19, X = OAc | 49 (21) | 29:1 |
| 6 | | | 20, X = Br | 48 (17) | 20:1 |
| 7 | H H  α R  O | HO H  R  O | 21, R = CH₃ | 52 (18) | >99:1 |
| 8 | | | 22, R = OCH₃ | 56 (32) | >99:1 |

*Unless otherwise noted, isolated yields are of pure major product isolated from the entire reaction mixture. †rsm = % recovered unoxidized starting material. ‡GC analysis of crude reaction mixture using authentic standards. §Isolated as a 1:1 mixture of remote:proximal.

FIG. 4

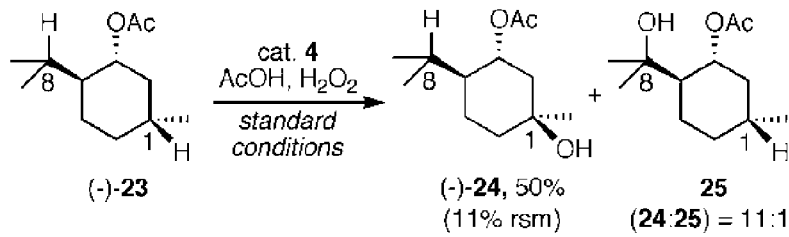

FIG. 5

I. electronic
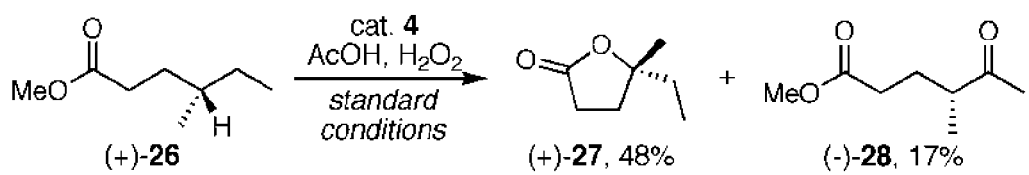
II. steric
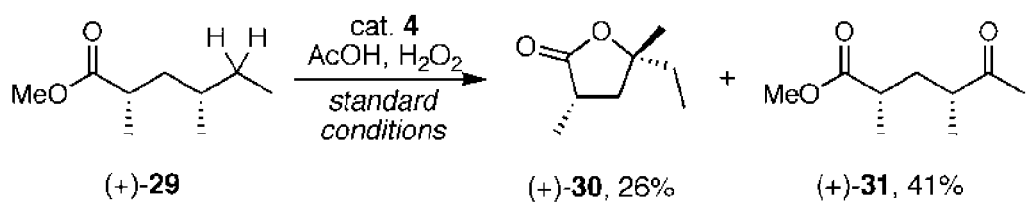
III. directed
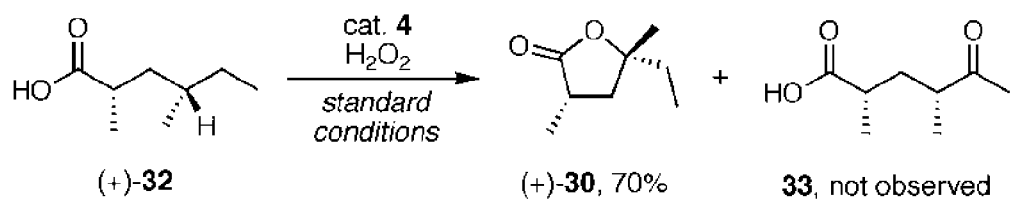
FIG. 6

SELECTIVE ALIPHATIC C—H OXIDATION

CROSS-REFERENCE TO RELATED APPLICATIONS

This application claims the benefit of U.S. Provisional Application No. 60/977,271 entitled "Selective Aliphatic C—H Oxidation" filed Oct. 3, 2007, which is incorporated by reference in its entirety.

BACKGROUND

Intricate organic molecules, such as synthetic and natural bioactive molecules, typically include a hydrocarbon skeleton containing a large number of aliphatic C—H bonds. Oxidized functionalities containing oxygen and/or nitrogen typically decorate the hydrocarbon skeleton. The identity and position of the oxidized functionalities within a molecule are believed to strongly affect the biological activity of the molecule. Thus, reactions that selectively introduce an oxidized functionality into an organic framework are of particular significance in the synthesis of bioactive molecules.

A few general reaction classes have emerged for introducing oxidized functionality into organic frameworks. These reaction classes include functional group interconversions, C—C bond forming reactions of pre-oxidized fragments, and olefin oxidations. Using these reactions, modern synthetic planning is often focused on the use and maintenance of oxidized functionalities once they have been introduced into the molecule.

In contrast, iron enzymes routinely perform catalytic, selective oxidations of isolated $sp^3$-hybridized C—H bonds in intricate molecules. Examples of these enzymes include cytochrome P-450 and methane monooxygenase (MMO). The selective reactivity of these natural catalysts is dependent on elaborate protein binding pockets. Although these binding pockets provide enzymes with good specificity and reactivity, they also limit the general applicability of the enzymes in the oxidation of a broad range of substrate molecules.

The paradoxical challenge in developing a useful oxidation reaction for intricate molecules is to provide a composition, such as a reagent and/or a catalyst, that is both highly reactive and predictably selective for oxidation of inert and ubiquitous C—H bonds. Moreover, to be useful in intricate molecule synthesis, the reaction preferably has a reactivity and a selectivity that are general for a broad range of substrates. Such a reaction could streamline complicated syntheses by providing a general way to install oxidized functionalities at a late-stage, thereby reducing unproductive chemical manipulations associated with carrying them throughout a synthetic procedure.

SUMMARY

In one aspect, the invention provides a composition including a complex having a structural formula selected from I, its (R,R) enantiomer and mixtures:

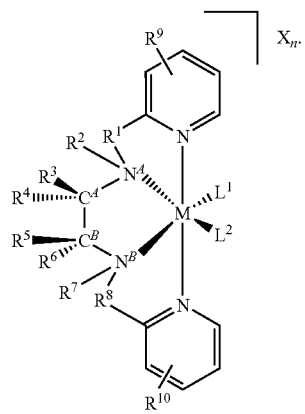

M is a metal; $L^1$ and $L^2$ are ancillary ligands; X is a counterion; n is 2 or 3; $R^1$, $R^2$, $R^7$ and $R^8$ independently are selected from the group consisting of an alkyl group, a heteroalkyl group, an aryl group and a heteroaryl group; $R^3$, $R^4$, $R^5$ and $R^6$ independently are selected from the group consisting of hydrogen, a halide group, an alkyl group, a heteroalkyl group, an aryl group and a heteroaryl group; $R^9$ and $R^{10}$ independently are selected from the group consisting of hydrogen, a halide group, an alkyl group, a heteroalkyl group, an aryl group, a heteroaryl group, a nitro group, and a group linking the complex to a surface; and where $C^A$ and $N^A$, in combination with at least one pair of groups selected from the group consisting of $R^1$ and $R^3$, $R^1$ and $R^4$, $R^2$ and $R^3$, and $R^2$ and $R^4$, form at least one ring.

In another aspect, the invention provides a composition including a complex having a structural formula selected from II, its (R,R) enantiomer and mixtures:

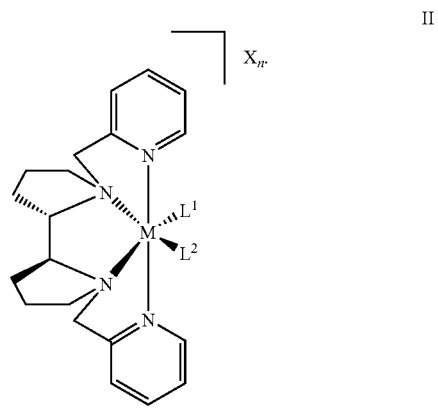

M is a metal selected from the group consisting of Fe(II), Fe(III), Mn(II) and Mn(III); $L^1$ and $L^2$ are ancillary ligands, where $L^1$ and $L^2$ independently are selected from acetone, acetonitrile and a μ-oxo bridge, or $L^1$ and $L^2$ together are a carboxylate group; X is a counterion selected from the group consisting of $Cl^-$, $Br^-$, $AcO^-$, $TfO^-$, $CF_3CO_2^-$, $BF_4^-$, $ClO_4^-$, $ReO_4^-$, $AsF_6^-$, and $SbF_6^-$; and n is 2 or 3.

In yet another aspect, the invention provides a method of oxidizing a substrate, including reacting a substrate and an oxidant in a first reaction mixture that includes a composition as described above, and providing an oxidized product in the first reaction mixture.

In yet another aspect, the invention provides a method of modeling the interaction of a cytochrome P-450 enzyme with a substrate, including reacting a substrate and an oxidant in a reaction mixture that includes a composition as described above; providing at least one oxidized product in the reaction mixture; and analyzing the at least one oxidized product.

In yet another aspect, the invention provides a catalyst including a complex of a metal, a tetradentate ligand, at least one ancillary ligand, and a counterion. When 0.005 mmol of the complex is combined with 19.8 mg cis-4-methylcyclohexyl pivalate and 3.0 mg acetic acid in 0.15 mL acetonitrile, and then treated dropwise at 25° C. over 45 seconds with 0.12 mmol $H_2O_2$ in 0.9 mL acetonitrile, the yield of trans-4-hydroxy-4-methylcyclohexyl pivalate after 15 minutes at 25° C. as determined by gas chromatography is at least 30%. The tetradentate ligand may include a N-heterocyclic-N,N'-bis (pyridyl)-ethane-1,2-diamine group. The tetradentate ligand may include a N,N'-bis(heterocyclic)-N,N'-bis(pyridyl)-ethane-1,2-diamine group.

The following definitions are included to provide a clear and consistent understanding of the specification and claims.

The term "complex" means a molecular entity including a central metal atom, to which is associated a surrounding array of other groups of atoms, referred to as "ligands."

The term "group" means a linked collection of atoms or a single atom within a molecular entity, where a molecular entity is any constitutionally or isotopically distinct atom, molecule, ion, ion pair, radical, radical ion, complex, conformer etc., identifiable as a separately distinguishable entity. The description of a group as being "formed by" a particular chemical transformation does not imply that this chemical transformation is involved in making the molecular entity that includes the group.

The term "alkyl group" means a group formed by removing a hydrogen from a carbon of an alkane, where an alkane is an acyclic or cyclic compound consisting entirely of hydrogen atoms and saturated carbon atoms. An alkyl group may be substituted with one or more substituent groups.

The term "heteroalkyl group" means a group formed by removing a hydrogen from a carbon of a heteroalkane, where a heteroalkane is an acyclic or cyclic compound consisting entirely of hydrogen atoms, saturated carbon atoms, and one or more heteroatoms. A heteroalkyl group may be substituted with one or more substituent groups.

The term "aryl group" means a group formed by removing a hydrogen from a ring carbon atom of an aromatic compound. An aryl group may be monocyclic or polycyclic and may include one or more heteroatoms in the ring and/or may be substituted with one or more substituent groups.

The term "aromatic compound" means a monocyclic or polycyclic aromatic hydrocarbon, optionally including one or more heteroatoms in the ring. An aromatic compound may be substituted with one or more substituent groups.

The term "heteroaryl group" means an aryl group that contains a heteroatom in the ring. A heteroaryl group may be monocyclic or polycyclic and may be substituted with one or more substituent groups.

The term "heterocyclic group" means a group formed by removing a hydrogen from a ring atom of a heterocyclic compound, where a heterocyclic compound is a cyclic compound having as ring members carbon and at least one other element. Heterocyclic groups include heterocycloalkyl groups, heteroaryl groups, and mixtures of these. A heterocyclic group may be monocyclic or polycyclic and may be substituted with one or more substituent groups.

The term "pyridyl group" means a group formed by removing a hydrogen from a ring atom of pyridine. A pyridyl group may be substituted with one or more substituent groups. Substituent groups of a pyridyl group may form a ring, in which case the pyridyl group is part of a polycylic heterocyclic group, such as a quinolinyl group.

The term "substituent group" means a group that replaces one or more hydrogen atoms in a molecular entity. Examples of substituent groups include halide groups, alkyl groups, heteroalkyl groups, aryl groups, heteroaryl groups, and nitro groups.

The term "halide group" means —F, —Cl, —Br or —I.

The term "oxidation" means a chemical transformation of a substrate molecule, where the oxidized product molecule of the chemical transformation includes at least one more oxygen atom and/or at least one fewer hydrogen atom than the original substrate molecule.

The term "oxidant" means a substance that provides at least one oxygen atom to, and/or accepts at least one hydrogen atom from, a substrate molecule in an oxidation reaction of the substrate.

The term "$sp^3$ C—H bond" means a C—H bond in which the carbon atom is bonded to three other atoms through individual single bonds.

BRIEF DESCRIPTION OF THE DRAWINGS

The invention can be better understood with reference to the following drawings and description. The components in the figures are not necessarily to scale, emphasis instead being placed upon illustrating the principles of the invention.

FIG. 1 represents chemical structures of two different complexes, and an X-ray crystal structure of one of the complexes (anions omitted for clarity).

FIG. 2 represents chemical structures, reaction schemes and reaction yields for an example of an oxidation of the substrate 4-methylcyclohexyl pivalate in the presence of two different complexes.

FIG. 4 represents chemical structures, reaction schemes and reaction yields for examples of oxidation reactions of similar substrates having 3° C—H bonds in a variety of electronic environments.

FIG. 5 represents chemical structures, reaction schemes and reaction yields for an example of an oxidation reaction of a substrate having two 3° C—H bonds in different steric environments.

FIG. 6 represents chemical structures, reaction schemes and reaction yields for examples of oxidation reactions of similar substrates having 3° C—H bonds in different combinations of electronic and steric environments.

DETAILED DESCRIPTION

Figure 3:
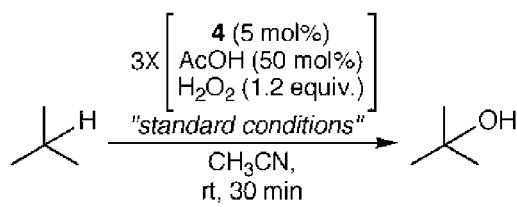
FIG. 3 represents chemical structures, reaction schemes and reaction yields for examples of oxidation reactions of a variety of organic substrates.

The present invention makes use of the discovery that site-selective $sp^3$ C—H bond oxidation can be predictably controlled in the presence of a sterically bulky and electrophilic complex. The novel class of complexes can use $H_2O_2$, an inexpensive and environmentally friendly oxidant, to effect highly selective oxidations of unactivated $sp^3$ C—H bonds over a broad range of substrates. The site of oxidation with the complexes can be predicted, based on the electronic and/or steric environment of the C—H bond. In addition, the oxidation reaction does not require the presence of directing groups in the substrate. Thus, the $sp^3$ C—H oxidation reaction can be used in a predictable fashion on intricate small molecule substrates to furnish oxidized products in preparatively useful yields.

A composition for selective $sp^3$ C—H bond oxidation may include a complex of a metal and a tetradentate ligand. The metal may be, for example, iron or manganese, including Fe(II), Fe(III), Mn(II) and Mn(III). The tetradentate ligand binds to the metal through four separate atoms, each of which independently may be a heteroatom. Preferably at least one of the binding atoms in the ligand is nitrogen, and more preferably all four binding atoms in the ligand are nitrogens. The complex may include at least one ancillary ligand for the metal, and may include a counterion.

In one example, a composition for selective $sp^3$ C—H bond oxidation may include a complex of a metal, a tetradentate ligand, at least one ancillary ligand, and a counterion, where the tetradentate ligand includes a N-heterocyclic-N,N'-bis (pyridyl)-ethane-1,2-diamine group. Each pyridyl group independently is substituted with one or more substituent groups, one of which is a group linking the pyridyl ring with one of the amine nitrogens. At least one amine nitrogen in the group is part of a heterocyclic group. If each amine nitrogen in the group is part of a heterocyclic group, then the group may be referred to as a N,N'-bis(heterocyclic)-N,N'-bis(pyridyl)-ethane-1,2-diamine group.

In another example, a composition for selective $sp^3$ C—H bond oxidation includes a complex having structural formula I, its (R,R) enantiomer, or a mixture of these:

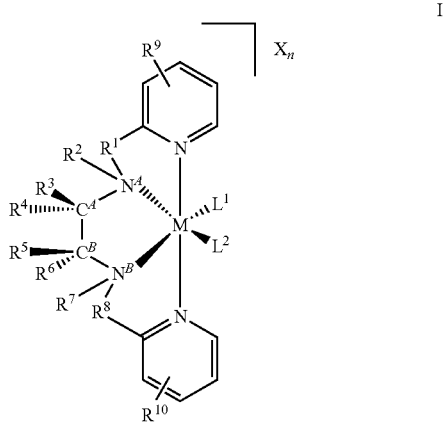

I

In this example, M is a metal; $L^1$ and $L^2$ are ancillary ligands; X is a counterion; n is 2 or 3; $R^1$, $R^2$, $R^7$ and $R^8$ independently are an alkyl group, a heteroalkyl group, an aryl group or a heteroaryl group; $R^3$, $R^4$, $R^5$ and $R^6$ independently are hydrogen (—H), a halide group, an alkyl group, a heteroalkyl group, an aryl group or a heteroaryl group; $R^9$ and $R^{10}$ independently are hydrogen, a halide group, an alkyl group, a heteroalkyl group, an aryl group, a heteroaryl group, a nitro group (—$NO_2$), or a group linking the complex to a surface. The superscripts "A" and "B" for $C^A$, $C^B$, $N^A$ and $N^B$ are used simply to identify which carbon and nitrogen atoms are included in a group within the structural formula. $C^A$ and $N^A$, in combination with $R^1$ and $R^3$, with $R^1$ and $R^4$, with $R^2$ and $R^3$, and/or with $R^2$ and $R^4$, form at least one ring.

The metal M may be Fe(II), Fe(III), Mn(II) or Mn(III). Preferably M is iron, and more preferably is Fe(II). The ancillary ligands $L^1$ and $L^2$ independently may be, for example, acetone, acetonitrile, or a μ-oxo bridge to another metal; or $L^1$ and $L^2$ together may be a single ligand, such as a carboxylate group, a diketone or a diamine. If one of $L^1$ and $L^2$ is a μ-oxo bridge to another metal, then the other of $L^1$ and $L^2$ preferably bridges the two metals also, either as another μ-oxo bridge, or as an organic bridge such as acetone, acetonitrile or a divalent ligand. Preferably $L^1$ and $L^2$ independently are acetonitrile or a μ-oxo bridge.

The counterion X may be any anion. Examples of counterions include $Cl^-$, $Br^-$, $AcO^-$, $TfO^-$, $CF_3CO_2^-$, $BF_4^-$, $ClO_4^-$, $ReO_4^-$, $AsF_6^-$, and $SbF_6^-$. The complex may include two or three counterions. The complex may further include a counterion that is present as a salt with a cation, providing an in situ anion exchange reagent. Examples of cations that may be present in a salt include $Na^+$, $Li^+$, $K^+$, $Cs^+$ and $Ag^+$.

The groups $R^1$, $R^2$, $R^7$ and $R^8$ independently are an alkyl group, a heteroalkyl group, an aryl group or a heteroaryl group. If $R^1$, $R^2$, $R^7$ or $R^8$ is an alkyl group or a heteroalkyl group, the group preferably includes from 1 to 20 carbon atoms, and more preferably includes from 1 to 10 carbon atoms, from 1 to 5 carbon atoms, from 1 to 3 carbon atoms, or from 1 to 2 carbon atoms. If $R^1$, $R^2$, $R^7$ or $R^8$ is an aryl group or a heteroaryl group, the group preferably includes from 5 to 20 carbon atoms, and more preferably includes from 5 to 12 carbon atoms, from 5 to 10 carbon atoms, from 5 to 9 carbon atoms, or from 5 to 6 carbon atoms.

$R^1$ may be —$C(R^{1a})(R^{1b})$—, where the $R^{1a}$ and $R^{1b}$ groups independently may be hydrogen, a halide group, an alkyl group, a heteroalkyl group, an aryl group or a heteroaryl group. At least one of $R^{1a}$ and $R^{1b}$ may be part of a ring. $R^2$ preferably is —$CH_3$, or is part of a ring.

$R^7$ preferably is —$CH_3$, or is part of a ring. $R^8$ may be —$C(R^{8a})(R^{8b})$—, where the $R^{8a}$ and $R^{8b}$ groups independently may be hydrogen, a halide group, an alkyl group, a heteroalkyl group, an aryl group or a heteroaryl group. At least one of $R^{8a}$ and $R^{8b}$ may be part of a ring.

The groups $R^3$, $R^4$, $R^5$ and $R^6$ independently are hydrogen, a halide group, an alkyl group, a heteroalkyl group, an aryl group or a heteroaryl group. If $R^3$, $R^4$, $R^5$ or $R^6$ is an alkyl group or a heteroalkyl group, the group preferably includes from 1 to 20 carbon atoms, and more preferably includes from 1 to 10 carbon atoms, from 1 to 5 carbon atoms, from 1 to 3 carbon atoms, or from 1 to 2 carbon atoms. If $R^3$, $R^4$, $R^5$ or $R^6$ is an aryl group or a heteroaryl group, the group preferably includes from 5 to 20 carbon atoms, and more preferably includes from 5 to 12 carbon atoms, from 5 to 10 carbon atoms, from 5 to 9 carbon atoms, or from 5 to 6 carbon atoms.

$R^3$ preferably is hydrogen or an alkyl group. More preferably, $R^3$ is an alkyl group that is part of a cycloalkyl ring or heterocycloalkyl ring, which is preferably a 5-membered ring. $R^4$ preferably is hydrogen or an alkyl group. More preferably, $R^4$ is an alkyl group that is part of a cycloalkyl ring or heterocycloalkyl ring, which is preferably a 5-membered ring. $R^5$ preferably is hydrogen or an alkyl group. More preferably, $R^5$ is an alkyl group that is part of a cycloalkyl ring or heterocycloalkyl ring, which is preferably a 5-membered ring. $R^6$ preferably is hydrogen or an alkyl group. More preferably, $R^6$ is an alkyl group that is part of a cycloalkyl ring or heterocycloalkyl ring, which is preferably a 5-membered ring.

As noted above, $C^A$ and $N^A$, in combination with $R^1$ and $R^3$, with $R^1$ and $R^4$, with $R^2$ and $R^3$, and/or with $R^2$ and $R^4$, form at least one ring. For example, $C^A$ and $N^A$ may form two rings, in which the $C^A$—$N^A$ bond is part of both rings. Likewise, $C^B$ and $N^B$, in combination with $R^8$ and $R^6$, with $R^8$ and $R^5$, with $R^7$ and $R^6$, and/or with $R^7$ and $R^8$, may form at least one ring. These rings independently may be heterocycloalkyl groups or heteroaryl groups, and may be substituted with one or more substituent groups. These rings independently may have from 4 to 20 ring atoms, preferably from 5 to 12 ring atoms, more preferably from 5 to 10 ring atoms, more preferably from 5 to 9 ring atoms, and more preferably from 5 to 6 ring atoms.

Similarly, $C^A$ and $C^B$, in combination with $R^3$ and $R^5$, with $R^4$ and $R^6$, with $R^4$ and $R^5$, and/or with $R^3$ and $R^6$, may form at least one ring. These rings independently may be cycloalkyl groups, heterocycloalkyl groups, aryl groups or heteroaryl groups, and may be substituted with one or more substituent groups. These rings independently may have from 4 to 20 ring atoms, preferably from 5 to 12 ring atoms, more preferably from 5 to 10 ring atoms, more preferably from 5 to 9 ring atoms, and more preferably from 5 to 6 ring atoms.

The groups $R^9$ and $R^{10}$ independently are hydrogen, a halide group, an alkyl group, a heteroalkyl group, an aryl group, a heteroaryl group, a nitro group, or a group linking the complex to a surface. If $R^9$ or $R^{10}$ is an alkyl group or a heteroalkyl group, the group preferably includes from 1 to 20 carbon atoms, and more preferably includes from 1 to 10 carbon atoms, from 1 to 5 carbon atoms, from 1 to 3 carbon atoms, or from 1 to 2 carbon atoms. If $R^9$ or $R^{10}$ is an aryl group or a heteroaryl group, the group preferably includes from 5 to 20 carbon atoms, and more preferably includes from 5 to 12 carbon atoms, from 5 to 10 carbon atoms, from 5 to 9 carbon atoms, or from 5 to 6 carbon atoms.

The groups $R^9$ and $R^{10}$ may be monovalent or divalent. If $R^9$ or $R^{10}$ is a divalent group, the group, together with the pyridyl group to which it is bonded, may form a polyaromatic ring group, such as a quinolinyl group. The pyridyl groups to which $R^9$ and $R^{10}$ are bonded independently may be substituted with one or more other substituent groups, such as a halide group, a nitro group, an alkyl group, a heteroalkyl group, an aryl group and/or a heteroaryl group.

$R^1$ and $R^9$, in combination with the atoms to which they are bonded, may form a ring. Such a ring may be a cycloalkyl ring or an aryl ring. Preferably such a ring, if present, is an aryl ring, in which case the pyridyl group may be part of a quinolinyl group. Likewise $R^3$ and $R^{10}$, together with the atoms to which they are bonded, may form a ring, which may be a cycloalkyl ring or an aryl ring. Preferably such a ring, if present, is an aryl ring, in which case the pyridyl group may be part of a quinolinyl group.

The tetradentate ligand in structural formula I is a N-heterocyclic-N,N'-bis(pyridyl)-ethane-1,2-diamine ligand. The ring including $C^A$ and $N^A$ is a heterocyclic ring. The pyridine ring substituted with substituent groups $R^1$ and $R^9$ is one pyridyl group, and the pyridine ring substituted with substituent groups $R^8$ and $R^{10}$ is another pyridyl group.

In one example of a complex having structural formula I and/or its enantiomer, $N^A$, $C^A$, $R^2$ and $R^4$ form a 5-membered heterocycloalkyl ring; and $N^B$, $C^B$, $R^5$ and $R^7$ form a 5-membered heterocycloalkyl ring. Such a complex, for example, may have structural formula II, its (R,R) enantiomer, or a mixture. In this example, $R^1$ and $R^8$ are —$CH_2$—; $R^3$, $R^6$, $R^9$ and $R^{10}$ are hydrogen; $N^A$, $C^A$, $R^2$ and $R^4$ form a 5-membered heterocycloalkyl ring; $N^B$, $C^B$, $R^5$ and $R^7$ form a 5-membered heterocycloalkyl ring; and M, $L^1$, $L^2$, X and n are as defined for structural formula I.

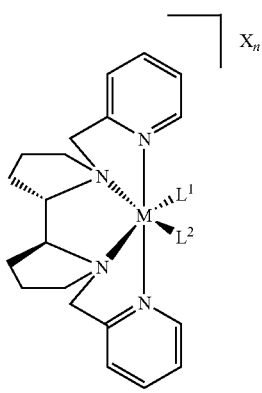

The tetradentate ligand in this complex is referred to as a (−)-2-((2-(1-(pyridin-2-ylmethyl)pyrrolidin-2-yl)pyrrolidin-1-yl)methyl)pyridine ligand, which may be abbreviated as PDP. The ligand may be in the (S,S) enantiomeric form as illustrated, or it may be in the (R,R) enantiomeric form.

In another example of a complex having structural formula I and/or its enantiomer, $N^A$, $C^A$, $R^1$ and $R^3$ form a 5-membered heterocycloalkyl ring; and $N^B$, $C^B$, $R^6$ and $R^8$ form a 5-membered heterocycloalkyl ring. Such a complex, for example, may have structural formula III and/or its enantiomer, in which $N^A$, $C^A$, $R^1$ and $R^3$ form a 5-membered heterocycloalkyl ring; $N^B$, $C^B$, $R^6$ and $R^8$ form a 5-membered heterocycloalkyl ring; $R^2$ and $R^7$ are —$CH_3$; $R^4$, $R^5$, $R^9$ and $R^{10}$ are hydrogen; and M, $L^1$, $L^2$, X and n are as defined for structural formula I.

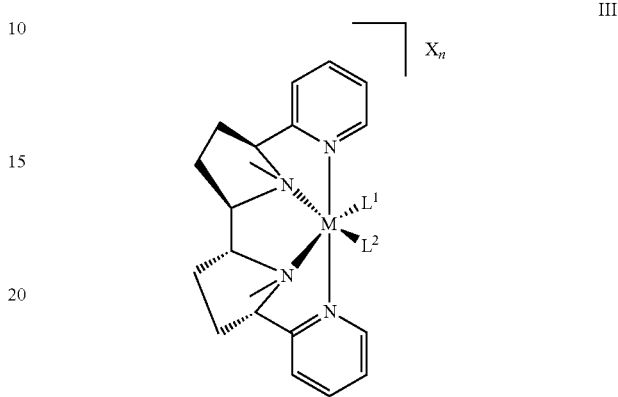

In another example of a complex having structural formula I and/or its enantiomer, $N^A$, $C^A$, $R^2$ and $R^4$ form a 5-membered heterocycloalkyl ring; and $N^B$, $C^B$, $R^5$ and $R^8$ form a 5-membered heterocycloalkyl ring. Such a complex, for example, may have structural formula IV and/or its enantiomer, in which $R^1$ is —$CH_2$—; $N^A$, $C^A$, $R^2$ and $R^4$ form a 5-membered heterocycloalkyl ring; $N^B$, $C^B$, $R^5$ and $R^8$ form a 5-membered heterocycloalkyl ring; $R^7$ is —$CH_3$; $R^3$, $R^6$, $R^9$ and $R^{10}$ are hydrogen; and M, $L^1$, $L^2$, X and n are as defined for structural formula I. The asterisks indicate a stereogenic carbon.

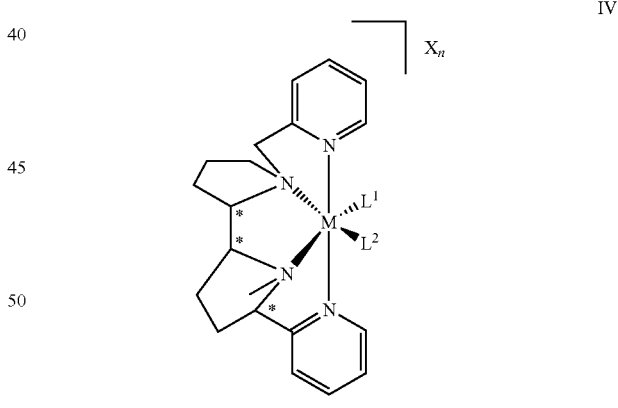

In another example of a complex having structural formula I and/or its enantiomer, $N^A$, $C^A$, $R^2$ and $R^4$ form a 5-membered heterocycloalkyl ring; $C^A$, $C^B$, $R^3$ and $R^5$ form a 5-membered cycloalkyl ring; and $N^B$, $C^B$, $R^5$ and $R^7$ form a 5-membered heterocycloalkyl ring. Such a complex, for example, may have structural formula V and/or its enantiomer, in which $R^1$ and $R^8$ are —$CH_2$—; $N^A$, $C^A$, $R^2$ and $R^4$ form a 5-membered heterocycloalkyl ring; $C^A$, $C^B$, $R^3$ and $R^5$ form a 5-membered cycloalkyl ring; $N^B$, $C^B$, $R^5$ and $R^7$ form a 5-membered heterocycloalkyl ring; $R^6$, $R^9$ and $R^{10}$ are hydrogen; and M, $L^1$, $L^2$, X and n are as defined for structural formula I.

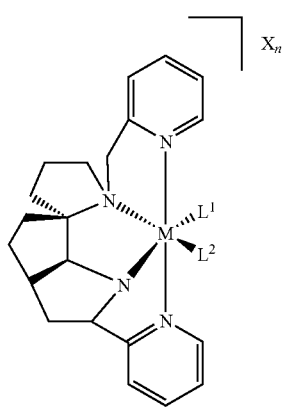

V

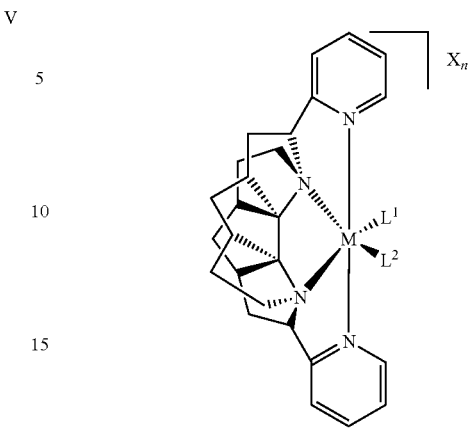

VII

In another example of a complex having structural formula I and/or its enantiomer, $N^A$, $C^A$, $R^2$ and $R^4$ form a 5-membered heterocycloalkyl ring; $C^A$, $C^B$, $R^4$ and $R^6$ form a 5-membered cycloalkyl ring; $C^A$, $C^B$, $R^3$ and $R^5$ form a 5-membered cycloalkyl ring; and $N^B$, $C^B$, $R^5$ and $R^7$ form a 5-membered heterocycloalkyl ring. Such a complex, for example, may have structural formula VI and/or its enantiomer, in which $R^1$ and $R^8$ are —CH$_2$—; $N^A$, $C^A$, $R^2$ and $R^4$ form a 5-membered heterocycloalkyl ring; $C^A$, $C^B$, $R^4$ and $R^6$ form a 5-membered cycloalkyl ring; $C^A$, $C^B$, $R^3$ and $R^5$ form a 5-membered cycloalkyl ring; $N^B$, $C^B$, $R^5$ and $R^7$ form a 5-membered heterocycloalkyl ring; $R^9$ and $R^{10}$ are hydrogen; and M, $L^1$, $L^2$, X and n are as defined for structural formula I.

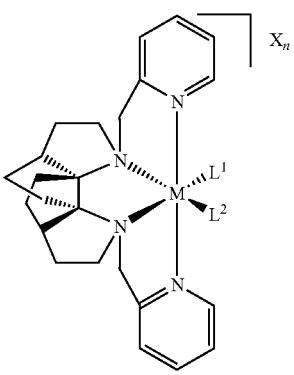

VI

In another example of a complex having structural formula I and/or its enantiomer, $N^A$, $C^A$, $R^1$ and $R^4$ form a 5-membered heterocycloalkyl ring; $N^A$, $C^A$, $R^2$ and $R^3$ form a 5-membered heterocycloalkyl ring; $C^A$, $C^B$, $R^4$ and $R^6$ form a 5-membered cycloalkyl ring; $C^A$, $C^B$, $R^3$ and $R^5$ form a 5-membered cycloalkyl ring; $N^B$, $C^B$, $R^5$ and $R^8$ form a 5-membered heterocycloalkyl ring; and $N^B$, $C^B$, $R^6$ and $R^7$ form a 5-membered heterocycloalkyl ring. Such a complex, for example, may have structural formula VII and/or its enantiomer, in which $N^A$, $C^A$, $R^1$ and $R^4$ form a 5-membered heterocycloalkyl ring; $N^A$, $C^A$, $R^2$ and $R^3$ form a 5-membered heterocycloalkyl ring; $C^A$, $C^B$, $R^4$ and $R^6$ form a 5-membered cycloalkyl ring; $C^A$, $C^B$, $R^3$ and $R^5$ form a 5-membered cycloalkyl ring; $N^B$, $C^B$, $R^5$ and $R^8$ form a 5-membered heterocycloalkyl ring; $N^B$, $C^B$, $R^6$ and $R^7$ form a 5-membered heterocycloalkyl ring; $R^9$ and $R^{10}$ are hydrogen; and M, $L^1$, $L^2$, X and n are as defined for structural formula I.

In all of the above structural formulas, the complex may be in the form as shown, or the complex may be in an enantiomeric form. A composition for selective sp$^3$ C—H bond oxidation may include a single enantiomer of a complex, or it may include a mixture of enantiomers of the complex.

A composition for selective sp$^3$ C—H bond oxidation may be used to introduce oxidized functionality into a molecule. A method of oxidizing a substrate may include reacting a substrate and an oxidant in a first reaction mixture that includes the composition, and providing an oxidized product in the first reaction mixture. The first reaction mixture may include a solvent and/or at least one additive. The oxidized product may include an oxidized functionality that was not present in the substrate. The method optionally may include collecting unoxidized substrate from the first reaction mixture, reacting the unoxidized substrate with an oxidant in a second reaction mixture that includes the composition, and providing the oxidized product in the second reaction mixture. The method optionally may include repeating, at least once, collecting unoxidized substrate, reacting the unoxidized substrate with the oxidant in a supplemental reaction mixture that includes the composition, and providing the oxidized product in the supplemental reaction mixture. The second reaction mixture and/or a supplemental reaction mixture independently may include a solvent and/or at least one additive.

The substrate may be any molecule that includes at least one sp$^3$ C—H bond. The substrate may be free of directing groups conventionally required for selective oxidation. The site on the substrate at which oxidation will occur may be predicted, based on the electronic and/or steric environment of the C—H bond.

The oxidant may be, for example, hydrogen peroxide (H$_2$O$_2$), ozone (O$_3$), a peracid, an alkyl hydroperoxide, or a periodinane. Examples of peracids include peracetic acid, m-chloroperbenzoic acid (mCPBA), and potassium peroxymonosulfate. Examples of alkyl hydroperoxides include t-butyl hydroperoxide and cumene hydroperoxide. Examples of periodinanes include iodosylbenzene (C$_6$H$_5$—I=O) and iodosobenzene diacetate (C$_6$H$_5$I(OOCCH$_3$)$_2$). Preferably the oxidant is H$_2$O$_2$.

Examples of solvents include acetonitrile, ethyl acetate, acetone and nitromethane. Preferably the solvent includes acetonitrile, either alone or as a mixture with ethyl acetate, acetone and/or nitromethane. Preferably the solvent is at least 50% by volume acetonitrile, and more preferably is 100% acetonitrile.

Examples of additives include alkyl carboxylic acids, such as formic acid, acetic acid, propionic acid, butyric acid, valeric acid, capric acid, oxalic acid, malonic acid, succinic acid, and glutaric acid. Preferably a reaction mixture includes acetic acid.

The reacting may include forming the first reaction mixture. The first reaction mixture includes the substrate, the oxidant and the composition, and may include a solvent and/or at least one additive. In one example, the reacting includes combining ingredients to form the first reaction mixture. The ingredients include the substrate, the oxidant and the composition, and may include a solvent and/or at least one additive. In another example, the reacting includes combining the substrate, the composition, the solvent and optionally an additive to form a first mixture, and then adding an oxidant mixture, including the oxidant and the solvent, to the first mixture to form the first reaction mixture. Preferably the oxidant mixture is added gradually, such as by a dropwise addition.

In one example, the reacting may further include adding a first supplemental composition mixture to the first reaction mixture, and then adding a first supplemental oxidant mixture to the first reaction mixture. The first supplemental composition mixture includes the composition, the solvent, and optionally an additive. The first supplemental oxidant mixture includes the oxidant and the solvent. Preferably the first supplemental oxidant mixture is added gradually, such as by a dropwise addition.

The reacting may further include adding a second supplemental composition mixture to the first reaction mixture, and then adding a second supplemental oxidant mixture to the first reaction mixture. The second supplemental composition mixture includes the composition, the solvent, and optionally an additive. The second supplemental oxidant mixture includes the oxidant and the solvent. Preferably the second supplemental oxidant mixture is added gradually, such as by a dropwise addition. Forming a first reaction mixture, followed by adding a first supplemental composition mixture and a first supplemental oxidant mixture, further followed by adding a second supplemental composition mixture and a second supplemental oxidant mixture, is referred to as a "three-fold reagent addition procedure".

The adding an oxidant mixture, adding a first supplemental oxidant mixture, and adding a second supplemental oxidant mixture independently may be performed gradually. Preferably the time elapsed during the addition of one or more of these mixtures is from 10 seconds to 10 minutes. More preferably the time elapsed during the addition of one or more of these mixtures is from 20 seconds to 5 minutes, more preferably from 30 seconds to 2 minutes, and more preferably from 45 to 75 seconds. Preferably the addition of the oxidant mixture and of the first and second supplemental oxidant mixtures includes a dropwise addition of the appropriate oxidant mixture.

The reaction time may be from 30 seconds to 2 hours per addition of reagents. Thus, the initial first reaction mixture may be maintained for 30 seconds to 2 hours before the first supplemental composition mixture and the first supplemental oxidant mixture are added, and then the first reaction mixture may be maintained for an additional 30 seconds to 2 hours before the second supplemental composition mixture and the second supplemental oxidant mixture are added. Preferably the reaction time is from 3 to 60 minutes per addition of reagents. For an oxidation that includes a three-fold reagent addition procedure, the total reaction time may be from 1.5 minutes to 6 hours, including from 9 minutes to 3 hours, from 15 minutes to 1 hour, and from 20 to 45 minutes.

The reacting may include maintaining the first reaction mixture at a temperature of from −20 to 36° C. Preferably the reaction temperature is from −10 to 35° C. More preferably the reaction temperature is from 5 to 30° C. The reaction temperature may be ambient temperature, from 20 to 30° C.

In an example of an oxidation method that includes a three-fold reagent addition procedure, a first mixture contains a substrate, the complex of structural formula I, a solvent and an additive. The substrate is present at a concentration of from 0.1 to 2 M, the complex is present at a level of from 1 to 15 mol % relative to the substrate, and the additive is present at a level of from 0.1 to 1 equivalent relative to the substrate. An oxidant mixture includes an oxidant and a solvent, at an oxidant concentration of from 0.05 to 0.5 M. The oxidant mixture is added dropwise to the first mixture over a period of from 45 to 75 seconds, to form the reaction mixture. The amount of oxidant is from 1 to 2 equivalents relative to the substrate. After the mixture has been stirred for 30 seconds to 2 hours at a temperature of from −20 to 36° C., a first supplemental composition mixture is added, followed by the gradual addition of a first supplemental oxidant mixture. The first supplemental composition mixture includes from 1 to 15 mol % of the complex in the solvent (0.01 to 0.1 M), and from 0.1 to 1 equivalent of the additive. The first supplemental oxidant mixture includes from 1 to 2 equivalents of the oxidant in the solvent (0.05 to 0.5 M). After the mixture has been stirred for 30 seconds to 2 hours at a temperature of from −20 to 36° C., a second supplemental composition mixture is added, followed by the gradual addition of a second supplemental oxidant mixture. The second supplemental composition mixture and the second supplemental oxidant mixture are as described for the first supplemental composition mixture and the first supplemental oxidant mixture, respectively.

In another example, the substrate is reacted with a composition and an oxidant using a three-fold reagent addition procedure, and the resulting reaction mixture includes an oxidized product and unoxidized substrate. At least a portion of the unoxidized substrate is collected from the reaction mixture. The collected unoxidized substrate is then reacted with the composition and the oxidant through another three-fold reagent addition procedure. The collection and subsequent reaction of unoxidized substrate is referred to as "recycling" the substrate. An oxidation reaction that includes a three-fold reagent addition procedure is referred to as an oxidation "cycle". Recycling the substrate may be performed one or more times.

In another example of an oxidation method, the reacting includes combining the substrate, the solvent and optionally an additive to form a substrate mixture, and then gradually adding both a composition mixture and an oxidant mixture to the substrate mixture, to form the reaction mixture. The composition mixture includes the composition, the solvent, and optionally an additive. The oxidant mixture includes the oxidant and the solvent. The gradual addition of both a composition mixture and an oxidant mixture is referred to as a "continuous reagent addition procedure".

In this example, the reaction time may be the time required for the composition mixture and the oxidant mixture to be combined in the reaction mixture. Preferably the reaction time is from 1.5 minutes to 6 hours, including from 9 minutes to 5 hours, from 15 minutes to 2 hours, and from 30 minutes to 1 hour. The time elapsed between forming the first mixture and beginning the continuous additions may be from 1 second to 10 minutes.

In an example of an oxidation method that includes a continuous reagent addition procedure, a substrate mixture contains a substrate, a solvent and an additive. The substrate is present at a concentration of from 0.1 to 2 M, and the additive is present at a level of from 0.01 to 1 equivalent relative to the substrate. A composition mixture contains the complex of structural formula I, the solvent, and the additive. The complex is present at a level of from 1 to 30 mol % relative to the substrate (0.01 to 1.0 M), and the additive is present at a level of from 0.1 to 1 equivalent relative to the substrate. An oxidant mixture includes an oxidant and the solvent, where the oxidant is present at a level of from 1 to 4 equivalents relative to the substrate (0.01 to 1.0 M). The composition mixture and the oxidant mixture are in separate syringes, each of which is loaded into a separate syringe pump. The composition mixture is gradually added to the substrate mixture, to form the reaction mixture, at a rate of from 0.01 to 0.1 mL/min. Once from 1 to 10 drops of the composition mixture has been added, the oxidant mixture is gradually added to the reaction mixture, at a rate of from 0.1 to 0.5 mL/min. The volumes, concentrations, and addition rates of the composition and oxidant mixtures may be set so that the addition of the oxidant mixture is completed from 0 to 10 minutes after the addition of the composition mixture is completed.

Providing an oxidized product preferably includes providing an oxidized product that includes a single oxidized functionality that was not present in the substrate. An oxidized product that includes a single oxidized functionality that was not present in the substrate is referred to as a "mono-oxidized product". Preferably providing an oxidized product includes providing mono-oxidized product with a yield of at least 50%. More preferably, providing an oxidized product includes providing mono-oxidized product with a yield of at least 60%, more preferably of at least 70%, more preferably of at least 80%, and more preferably of at least 90%. These yields may be the yields after an oxidation involving a three-fold reagent addition procedure or a continuous reagent addition procedure.

An oxidation reaction also may yield one or more oxidized products that include two or more oxidized functionalities that were not present in the substrate. Preferably, only minimal amounts of these multi-oxidized products are formed. Preferably less than 30% of the substrate is converted into a multi-oxidized product. More preferably, less than 20% of the substrate is converted into a multi-oxidized product, more preferably less than 10%, more preferably less than 5%, and more preferably less than 1%. Preferably a substrate molecule is either converted into the mono-oxidized product or is unoxidized.

FIG. 1 represents chemical structures of two different complexes. Complex 3 is conventional iron complex [Fe(II)(mep)(CH$_3$CN)$_2$](SbF$_6$)$_2$, where "mep" is N,N'-dimethyl-N,N'-bis(2-pyridylmethyl)-ethane-1,2-diamine. Complex 4 is [Fe(S,S-PDP)(CH$_3$CN)$_2$](SbF$_6$)$_2$, where PDP=2-((-2-(-1-(pyridin-2-ylmethyl)pyrrolidin-2-yl)pyrrolidin-1-yl)methyl)pyridine. The structure shown for 4 is based on the X-ray crystal structure illustrated, where the anions were omitted for clarity. Complex 4 corresponds to structural formula II, in which M is Fe(II), $L^1$ and $L^2$ are acetonitrile, X is SbF$_6^-$, and n is 2.

FIG. 2 represents chemical structures, reaction schemes and reaction yields for an example of an oxidation of the substrate 4-methylcyclohexyl pivalate in the presence of two different complexes. Experimental details are provided in Examples 3 and 4. Reaction of the substrate with complex 4 in the presence of acetic acid (AcOH) yielded 38% (by GC) of the mono-oxidized product 4-hydroxy-4-methylcyclohexyl pivalate (entry 4). This yield was amplified by using a three-fold reagent addition procedure, in which each addition of the complex included 5 mol % complex 4 and 0.5 equivalent AcOH, and each addition of oxidant included 1.2 equivalents H$_2$O$_2$. The three-fold reagent addition procedure was carried out over a period of 30 minutes, providing diastereomerically pure hydroxylated product 2 in 51% isolated yield (entry 5).

In comparison, reaction of the substrate with conventional iron complex 3 yielded only trace hydroxylated product (7%, entry 1). The addition of acetic acid resulted in a notable increase in yield of product 2 (entry 3) with substantial quantities of unoxidized starting material (approximately 59%). Using a three-fold reagent addition procedure, with 5 mol % complex 3, 0.5 equivalent AcOH and 1.2 equivalents H$_2$O$_2$ per addition over a period of 30 minutes, resulted in significantly higher yields of product 2 (44% GC yield, 42% isolated yield). Increasing initial complex loadings or adding more H$_2$O$_2$ alone gave no substantial change in conversion or yield, suggesting that inactivation may be the limiting factor in the reactivity of complex 3.

One possible explanation for the increased reactivity of complex 4 relative to complex 3 is that the ligand of complex 4 has an increased rigidity relative to the "mep" ligand of complex 3. It has been reported that the instability of iron complexes of "mep" towards oxidative conditions may be related to the flexibility of the "mep" ligand. The pyrrolidyl rings are believed to provide a more rigid ligand structure than do the N-methyl groups of the "mep" ligand.

These comparative reactions demonstrated that, when 0.005 mmol of a complex of a metal, a tetradentate ligand, at least one ancillary ligand, and a counterion is combined with 19.8 mg cis-4-methylcyclohexyl pivalate and 3.0 mg acetic acid in 0.15 mL acetonitrile, and then treated dropwise at 25° C. over 45 seconds with 0.12 mmol H$_2$O$_2$ in 0.9 mL acetonitrile, the yield of trans-4-hydroxy-4-methylcyclohexyl pivalate after 15 minutes at 25° C. as determined by gas chromatography is at least 30%. Preferably the yield of trans-4-hydroxy-4-methylcyclohexyl pivalate after 15 minutes as determined by gas chromatography is at least 35%, and more preferably is at least 38%. The tetradentate ligand may include a N-heterocyclic-N,N'-bis(pyridyl)-ethane-1,2-diamine group. Preferably the tetradentate ligand includes a N,N'-bis(heterocyclic)-N,N'-bis(pyridyl)-ethane-1,2-diamine group. More preferably the tetradentate ligand includes a (−)-2-((2-(1-(pyridin-2-ylmethyl)-pyrrolidin-2-yl)pyrrolidin-1-yl)methyl)pyridine group.

FIG. 3 represents chemical structures, reaction schemes and reaction yields for examples of oxidation reactions of a variety of organic substrates. These reactions demonstrated the selective, electrophilic nature of the oxidant generated with complex 4 and H$_2$O$_2$. In each example, hydroxylation occurred preferentially at the most electron rich 3° C—H bond, despite the fact that secondary C—H bonds have a significant statistical advantage (see entries 1-9). For entry 10, the cyclohexane substrate included no available 3° C—H bonds. In this example, oxidation occurred at the methylene hydrogens to afford the ketone product. Experimental details, including the definition for "standard conditions" as used in FIG. 3, are provided in Example 5.

These oxidation reactions with complex 4 were stereospecific. For entries 6 and 7, the 3° C—H bond was part of a stereogenic center, and hydroxylation was stereospecific. When coupled to asymmetric alkylation methods for constructing stereogenic 3° alkyl centers, this reaction may provide a highly simplifying transform for accessing optically pure tertiary alcohols.

These oxidation reactions with complex 4 were selective. For each entry, the mono-oxidized product and unoxidized substrate accounted for 72 to 100% of the original substrate. Thus, significant levels of indiscriminate oxidation were not incurred. Surprisingly, with a highly oxidized L-leucinol derivative, hydroxylation occurred exclusively at the 3° C—H bond (entry 8). Recycling of the starting material was done up to five times to obtain a 91% isolated yield of pure (−)-12.

These oxidation reactions with complex 4 were highly reactive. The major mono-oxidized products were furnished in preparatively useful isolated yields averaging above approximately 50% (33-92%). Surprisingly, these yields were the highest yields ever reported for a non-directed sp$^3$ C—H oxidation reaction on a wide range of substrates. For example, for entries 4 and 5 of FIG. 3, products 8 and 9 were provided at isolated yields of 43% and 52%, respectively. In contrast, under the same reaction conditions, conventional complex [Fe(II)(mep)(CH$_3$CN)$_2$](SbF$_6$)$_2$ (3) provided isolated yields of only 35% and 45%, respectively.

Although the dicationic iron complex 4 is Lewis acidic, a surprisingly broad range of moderately Lewis basic groups were well-tolerated. For example, cyclic ethers, esters, carbonates and electron-deficient amides were compatible with this C—H oxidation reaction. The site-selectivities and stereospecificities of oxidations with complex 4 were consistent with a concerted mechanism mediated by an electrophilic oxidant.

The selectivity of oxidation of a substrate with a composition for selective sp$^3$ C—H bond oxidation can be affected by three separate factors. One possible selectivity factor is the electronic environment of the sp$^3$ C—H bonds of the substrate. A second possible selectivity factor is the steric environment of the sp$^3$ C—H bonds of the substrate. A third possible selectivity factor is the presence or absence of directing groups in the substrate. One advantage of oxidation with a composition for selective sp$^3$ C—H bond oxidation is that high selectivities can be obtained without directing groups in the substrate. However, the ability to utilize directing groups may provide selectivities that are different or better than those provided by the electronic and/or steric environments alone. Each of these selectivity factors may be used as a handle for predicting the selectivity of a catalytic oxidation of a substrate.

FIG. 4 represents chemical structures, reaction schemes and reaction yields for examples of oxidation reactions of similar substrates having 3° C—H bonds in a variety of electronic environments. A series of dihydrocitronellol derivatives having electron withdrawing groups (EWGs) α- or β- to one of the two 3° C—H centers were evaluated. In substrates with no EWGs, equimolar mixtures of hydroxylated products at both centers were formed (entry 1). In the other examples, hydroxylation with complex 4 and H$_2$O$_2$ occurred preferentially at the 3° C—H bond remote from the EWGs (entries 2-8). β-Acetate or halogen functionalities gave modest but useful site-selectivities (entries 2-4), and α-electron withdrawing functionalities resulted in excellent selectivities for remote hydroxylation (entries 5, 6). Surprisingly, site-selectivities of >99:1 were observed when strongly electron-withdrawing carbonyls were incorporated α- to one of the 3° C—H bonds (entries 7, 8). These results demonstrated that C—H oxidations with complex 4 were subject to electronic deactivation with α- and β-EWGs. Thus, the electronic environment can provide a first handle for selectivity. Experimental details are provided in Example 6, and the definition for "standard conditions" as used in FIG. 4 is provided in Example 5.

FIG. 5 represents chemical structures, reaction schemes and reaction yields for an example of an oxidation reaction of a substrate having two 3° C—H bonds in different steric environments. The substrate (−)-acetoxy-p-menthane 23 was analyzed for energy-minimization at the DFT ab initio level (B3LYP/6-31G*), followed by calculation of the electrostatic atomic partial charges. In the lowest potential energy conformer of (−)-23, the two 3° C—H bonds in the gamma position relative to the acetate group (C-1 and C-8) were the least positive and had very similar atomic charges, suggesting a high similarity in their electron densities. Thus, based on only electronic factors, equivalent levels of oxidation would be predicted at these sites.

Surprisingly, oxidation at the C-1 site was strongly preferred. One possible explanation for this selectivity is that these bonds exist in very different steric environments. The gem-dimethyl groups of the isopropyl unit of energy-minimized (−)-23 are oriented away from the acetate moiety to relieve unfavorable steric interaction. This places the 3° C—H bond of C-8 proximal to the acetate group, making it sterically less accessible to the oxidant than the C-1 bond. Thus, in substrates where C—H bonds of similar electron densities are present, sterics can provide a second handle for selectivity. Experimental details are provided in Example 7, and the definition for "standard conditions" as used in FIG. 5 is provided in Example 5.

FIG. 6 represents chemical structures, reaction schemes and reaction yields for examples of oxidation reactions of similar substrates having 3° C—H bonds in different combinations of electronic and steric environments. Hexanoate (+)-26 was hydroxylated by complex 4 and H$_2$O$_2$ predominately at the 3° C—H site to afford, after an in situ lactonization, (+)-27 as the major product, with methyl ketone (−)-28 as the minor product. This outcome is consistent with the electronic effects on selectivity outlined above. Increasing the steric bulk around this site by introducing a second methyl substituent in substrate (+)-29 reversed the selectivity and resulted in formation of methyl ketone (+)-31 as the major product. It is interesting to note that 2° C—H bond oxidation by complex 4 also occurred at the most electron rich, least sterically hindered site. Thus, steric effects can override electronic effects in oxidation selectivities with complex 4. Oxidation at 2° C—H sites may operate with selectivities similar to those outlined above for 3° C—H sites. Experimental details are provided in Examples 8 and 9, and the definition for "standard conditions" as used in FIG. 6 is provided in Example 5.

The yields of the major products in the reactions of FIG. 6 were surprisingly high. For example, for the oxidation of (+)-29, major product (+)-31 was provided at an isolated yield of 41%. In contrast, under the same reaction conditions, conventional complex [Fe(II)(mep)(CH$_3$CN)$_2$](SbF$_6$)$_2$ (3) provided an isolated yield of only 18%.

Referring still to FIG. 6, the selectivity of oxidation with complex 4 can also be affected by a directing group. Reaction of complex 4 and H$_2$O$_2$ with hexanoic acid (+)-32 furnished only the 5-membered ring lactone (+)-30 in 70% isolated yield, whereas oxidation of the analogous methyl ester (+)-29 gave methyl ketone (+)-31 as the major product. The terminal carboxylic acid moiety in (+)-32 overrode the previously noted steric effects and directed hydroxylation to the hindered 3° site. Thus, a directing group may be used to provide a third handle for selectivity. Experimental details are provided in Example 10.

Figure 7:
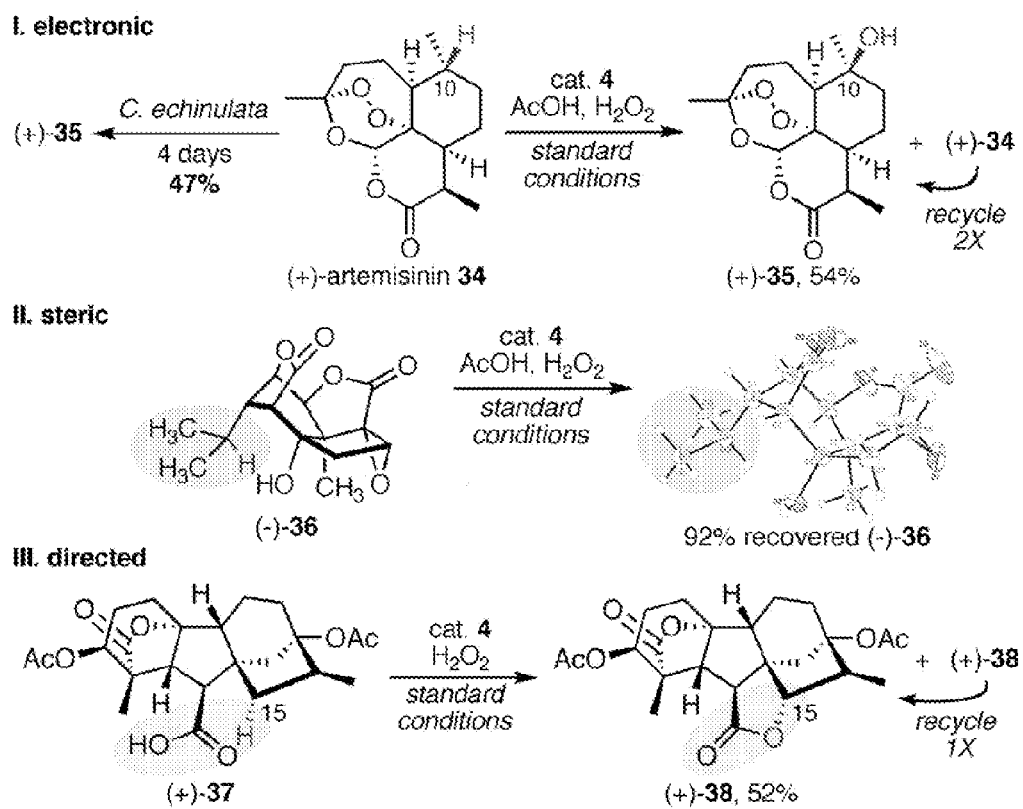
FIG. 7 represents chemical structures, reaction schemes and reaction yields for examples of oxidation reactions of a variety of natural products.

FIG. 7 represents chemical structures, reaction schemes and reaction yields for examples of oxidation reactions of a variety of natural products. As noted above, the selectivity of oxidation of a substrate with a composition for selective sp$^3$ C—H bond oxidation can be predicted by electronics, sterics, and/or a directing group. The predictability of the reaction selectivity can be advantageous in a variety of applications, including late-stage synthesis of bioactive molecules. The products of the oxidation reactions of FIG. 7 were consistent with these three selectivity factors. Compositions for selective sp$^3$ C—H bond oxidation may find widespread use for oxidative modifications to the core structures of natural products and drugs.

Antimalarial compound (+)-artemisinin 34 displays five 3° C—H bonds along its tetracyclic skeleton. In addition to the site-selectivity issue posed in this substrate, a chemoselectivity challenge was present in the form of a sensitive endoperoxide moiety known to be prone to Fe(II)-mediated cleavage. Based on the selectivity rules outlined above, the electron rich and sterically unencumbered 3° C—H bond at C-10 should be oxidized preferentially. The remaining 3° C—H bonds were α- and/or β- to electron-withdrawing ester and endoperoxide moieties. The predictability of the reaction selectivity was confirmed by the production of (+)-10b-hydroxyartemisinin 35 as the major product in 34% yield. By recycling this valuable starting material through the reaction twice, diastereomerically pure (+)-35 was obtained in 54% isolated yield. Thus, the selectivity rules observed with relatively simple substrates extended to this complex natural product. Experimental details are provided in Example 11, and the definition for "standard conditions" as used in FIG. 7 is provided in Example 5.

The 54% yield of (+)-35 was surprisingly high. Under the same reaction conditions, including recycling the starting material twice, conventional complex [Fe(II)(mep)(CH$_3$CN)$_2$](SbF$_6$)$_2$ (3) provided an isolated yield of only 22%. In addition, complex 4 provided only 8% recovered starting material; whereas complex 3 provided 40% recovered starting material.

Oxidation of (+)-34 with complex 4 also was an overall improvement relative to the enzymatic biotransformation of (+)-34 to (+)-35 with microbial cultures of Cunninghamella echinulata (J. Zhan et al. Tetrahedron Lett. 43, 4519 (2002)). The yield of 54% with complex 4 was higher than the 47% yield with the enzymatic process. The reaction time with complex 4 was significantly shorter than reaction time of four days with the enzymatic process. The volume throughput of 0.033M with complex 4 was ten-fold higher than the volume throughput of 0.0035M with the enzymatic process. The ability of a simple, small molecule complex with broad substrate scope to achieve selectivities comparable or better than cytochrome P450 enzymes is surprising and unexpected.

The sensitivity of complex 4 to steric effects was illustrated by its low reactivity toward (−)-α-dihydropicrotoxinin 36. All of the C—H bonds on the highly oxygenated core are electronically deactivated towards oxidation. Based on electronic factors alone, the 3° C—H bond of the exocyclic isopropyl moiety should have undergone selective oxidation with complex 4 and H$_2$O$_2$. However, treating (−)-36 under standard hydroxylation conditions resulted in 92% recovered starting material. The X-ray structure of (−)-36 revealed that the isopropyl moiety, in order to avoid severe unfavorable steric interactions, was oriented with its gem-dimethyl groups projecting away from the ring system. This oriented the isopropyl 3° C—H bond underneath the ring and rendered it inaccessible to complex 4. Experimental details are provided in Example 12.

The low reactivity of complex 4 with (−)-36 serves to highlight the large role steric factors can play in determining reactivity of C—H bonds with complex 4. Moreover, the low reactivity demonstrated that the complex and reaction conditions are mild. The substrate was a densely functionalized natural product derivative, but was only sparingly oxidized.

A powerful application of oxidation with complex 4 is to effect carboxylate-directed, diastereoselective lactonizations at 2° C—H sites. The carboxylate moiety of tetrahydrogibberellic acid analog (+)-37 may direct 5-membered ring lactonizations by complex 4 to one of four C—H bonds. Based on X-ray crystallographic analysis of (+)-37, hydroxylation should occur selectively at the 15α 2° C—H bond on the D-ring that is closest to the carboxylate moiety. The predictability of the reaction selectivity was confirmed by production of the 5-membered ring lactone (+)-38 as a single diastereomer in 52% isolated yield, after recycling the starting material once. Significantly, oxidation of the corresponding methyl ester of 37 resulted in mostly recovered starting material and mixtures of undefined oxidation products, none of which was (+)-38. Experimental details are provided in Example 13.

The yield of (+)-38 with complex 4 was surprisingly high. For a single reagent treatment (no recycling), the isolated yield was 41%, with 38% recovered starting material. Under the same reaction conditions, conventional complex [Fe(II)(mep)(CH$_3$CN)$_2$](SbF$_6$)$_2$ (3) provided an isolated yield of only 20%, with 51% recovered starting material.

A composition for selective sp$^3$ C—H bond oxidation may be used as a model of a cytochrome P450 enzyme to study, predict and/or design the biological metabolism of a substance. Cytochrome P-450 enzymes can be used to perform metabolic profiling of bioactive agents such as pharmaceuticals, additives to food and consumer products, and pollutants (Schmidt, B. et al. Biochem. Soc. Trans. 34(6), pp. 1241-1245 (2006)). Metabolic profiling typically includes contacting a substance with at least one cytochrome P-450 enzyme, and analyzing the reaction product(s). A reaction product may be analyzed, for example, for toxicity.

Cytochrome P-450 enzymes also have been used in the design of pro-drug molecules, which are molecules that are converted into an active pharmaceutical upon metabolization. Pro-drug design typically includes contacting a pro-drug candidate with at least one cytochrome P-450 enzyme, and analyzing the reaction product(s). A reaction product may be analyzed, for example, for therapeutic efficacy.

A method of modeling the interaction of a cytochrome P-450 enzyme with a substrate includes reacting a substrate and an oxidant in a reaction mixture that includes a composition, to provide at least one oxidized product, and analyzing the at least one oxidized product. The reaction mixture may include a solvent and/or at least one additive. The composition may be a composition for selective sp$^3$ C—H bond oxidation. The oxidized product may include an oxidized functionality that was not present in the substrate. Preferably the oxidized product is a mono-oxidized product. The substrate may be, for example, a bioactive agent or a pro-drug. Analyzing the at least one oxidized product may include, for example, determining the toxicity of the product or determining the therapeutic efficacy of the product.

Modeling the interaction of a cytochrome P-450 enzyme using a composition for selective sp$^3$ C—H bond oxidation may provide a number of advantages. Cytochrome P-450 enzyme studies typically require whole biological cells and enzyme cofactors. In contrast, oxidation with a selective composition can be performed with standard solvents and reagents. An individual cytochrome P-450 enzyme typically oxidizes only a narrow range of substrates. In contrast, a selective composition can predictably oxidize a broad range of substrates. Cytochrome P-450 enzyme studies typically require large reaction volumes, long reaction times on the order of days, and/or product yields below 50%. In contrast, oxidation with a selective composition can be performed in milliliter volumes, within 20 to 45 minutes, and with product yields of 50% or more.

Unactivated sp³ C—H bonds can be predictably oxidized by a small molecule metal complex without the benefit of elaborate catalyst binding pockets or substrate directing groups. A single complex can be used across a wide range of complex small molecules to provide selective C—H oxidation, which may be based solely on the electronic and steric properties of the substrate. This general C—H oxidation reaction has the potential to fundamentally alter the ways in which intricate molecules and drugs are synthesized in the laboratory.

The following examples are provided to illustrate one or more preferred embodiments of the invention. Numerous variations may be made to the following examples that lie within the scope of the invention.

EXAMPLES

Materials and Methods

The following commercially obtained reagents were used as received: 50% $H_2O_2$ (Sigma-Aldrich), AcOH (Mallinckrodt), $CH_3CN$ (Sigma-Aldrich). All oxidation reactions were run under air with no precautions taken to exclude moisture. All other reactions were run under a stream of $N_2$ gas unless otherwise stated.

Achiral gas chromatographic (GC) analyses were performed on Agilent Technologies 6890N Series instrument equipped with FID detectors using a HP-5 (5%-Phenyl)-methylpolysiloxane column (30 m, 0.32 mm, 0.25 μm). Chiral GC analysis was performed on an Agilent 5890 Series instrument equipped with FID detectors using a J&W cyclodex-β column (30 m, 0.25 mm, 0.25 μm). Thin-layer chromatography (TLC) was conducted with E. Merck silica gel 60 F254 precoated plates (0.25 mm) and visualized with UV, potassium permanganate, ceric ammonium molybdate, or vanillin staining. Flash column chromatography was performed as described by Still et al. (Still, W. C.; Kahn, M.; Mitra, A. *J. Org. Chem.* 1978, 43, 2923) using EM reagent silica gel 60 (230-400 mesh).

¹HNMR spectra were recorded on a Varian Unity-400 (400 MHz) or Varian Unity-500 (500 MHz) spectrometer and are reported in ppm using solvent as an internal standard ($CDCl_3$ at 7.26 ppm). Data reported as: s=singlet, d=doublet, t=triplet, q=quartet, m=multiplet, b=broad, app=apparent; coupling constant(s) in Hz; integration. Proton-decoupled ¹³C-NMR spectra were recorded on a Varian Unity-400 (100 MHz) or Varian Unity-500 (125 MHz) spectrometer and are reported in ppm using solvent as an internal standard ($CDCl_3$ at 77.0 ppm). ¹⁹F-NMR spectra were recorded on a Varian Unity-400 (376 MHz) and referenced externally using $FCCl_3$ as a standard (0 ppm).

Mass spectra were obtained through the Mass Spectrometry Laboratory, School of Chemical Sciences, University of Illinois. Chemical ionization (CI) spectra were performed on a Waters 70-VSE spectrometer using methane as the carrier gas. Electrospray ionization (ESI) spectra were performed on a Waters Q-T of Ultima spectrometer.

IR spectra were recorded as thin films on NaCl plates on a Mattson Galaxy Series FTIR 5000 and are reported in frequency of absorption ($cm^{-1}$). Optical rotation was measured using a 1 mL cell with a 1 dm path length on a Perkin-Elmer 341 polarimeter or using a 1 mL cell with a 5 cm path length on a Jasco DIP-360 digital polarimeter. Optical rotations were obtained with a sodium lamp and are reported as follows: $[\alpha]_\lambda^{ToC}$ (c=g/100 mL, solvent).

Example 1

Synthesis of (−)-2-(((S)-2-((S)-1-(pyridin-2-ylmethyl)pyrrolidin-2-yl)pyrrolidin-1-yl)methyl)pyridine (PDP)

A 200 mL round bottom flask was charged with a stir bar, (S,S)-2,2'-bispyrrolidine tartrate (Denmark, S. E.; Fu, J.; Lawler, M. J. *Org Syn*. 2006, 83, 121) (1.0 equiv, 4.0 g, 13.8 mmol) and $H_2O$ (30 mL), and $CH_2Cl_2$ (30 mL). Solid NaOH pellets (6.4 equiv, 3.53 g, 88.2 mmol) were added, followed by 2-picolyl chloride.HCl (2.2 equiv, 4.97 g, 30.3 mmol). After 18 h stirring at room temperature, the reaction mixture was diluted with 1M NaOH. The aqueous layer was extracted with $CH_2Cl_2$ (3×50 mL), and the organic extracts were combined, dried over $MgSO_4$, and concentrated in vacuo. The crude ligand thus obtained was purified by silica gel chromatography (5% MeOH/2% $NH_4OH/CH_2Cl_2$) and the collected fractions were combined, washed with 1M NaOH, dried over $MgSO_4$, and concentrated in vacuo to provide 2.8 g (8.6 mmol) of (S,S')-PDP in 62% isolated yield.

Example 2

Synthesis of $[Fe(S,S-PDP)(CH_3CN)_2](SbF_6)_2$ (4)

-continued

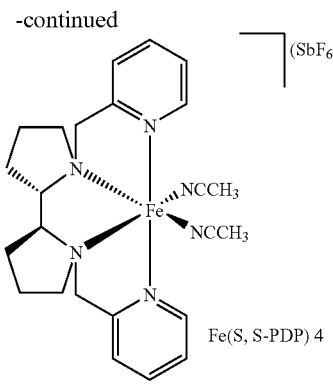

Fe(S, S-PDP) 4

A 50-mL round bottom flask was charged with (S,S)-PDP ligand (1.095 g, 3.39 mmol, 1 equiv.), and 20 mL $CH_3CN$. $Fe(II)Cl_2 \cdot 4H_2O$ (675 mg, 3.39 mmol, 1 equiv) was added to the stirring solution at room temperature under a nitrogen atmosphere. Immediately upon adding the Fe source to the (S,S)-PDP solution, precipitation of a bright orange solid was observed. Upon stirring for 24 h, diethyl ether was added to the solution to precipitate out the remainder of the complex. The solvent was decanted out of the flask via pipette and the solids were washed thoroughly with ether, and dried under a nitrogen stream for 4 hours to yield $Fe(S,S-PDP)(Cl)_2$ (1.29 g, 2.67 mmol, 79% yield): HRMS (ESI) m/z calc'd $C_{20}H_{26}N_4ClFe$ $[M-Cl]^+$: 413.1195, found 413.1201.

A flame dried 250-mL flask was charged with 608 mg of solid $Fe(S,S-PDP)(Cl)_2$ (1.35 mmol, 1 equiv.) suspended in $CH_3CN$ (17 mL) under nitrogen. Silver hexafluoroantimonate ($AgSbF_6$, 930 mg, 2.71 mmol, 2 equiv.) was weighed under an inert argon atmosphere and then added to the vigorously stirred heterogeneous mixture. The flask was covered with aluminum foil to protect the silver salts from light. After 16-24 hours, the reaction was filtered through Celite® and concentrated under vacuum. The purple solid was redissolved in $CH_3CN$, filtered through a 0.2 µm Acrodisc® LC PVDF filter (HPLC certified), and concentrated. The purple residue was redissolved in $CH_3CN$ and the filtration/concentration procedure was repeated two more times to ensure no silver salts remained. The purple solid obtained was dried under a nitrogen stream for 5 hours to yield $[Fe(II)(S,S-PDP)(CH_3CN)_2]$ $(SbF_6)_2$ (complex 4) (2.7 g, 3.08 mmol, quantitative yield).

X-ray quality crystals were obtained by dissolving 11.6 mg of complex 4 (0.0125 mmol) in a minimal amount of acetonitrile (0.1 mL). The vial containing this solution was placed, loosely capped, in a larger vial containing ether in order to promote the crystallization upon ether diffusion. Crystals were isolated after ca. 24 hours of slow evaporation. FIG. 1 includes a representation of the X-ray crystal structure of complex 4, where the anions were omitted for clarity.

Example 3

Oxidation of cis-4-methylcyclohexyl Pivalate (1) with a Single Addition of Complex A 4 mL screwtop vial was charged with the following: Fe complex (0.005 mmol, 5 mol %), cis-4-methylcyclohexyl pivalate (19.8 mg, 0.1 mmol, 1.0 equiv.), $CH_3CN$ (0.15 mL), AcOH (3.0 mg, 0.05 mmol, 50 mol %), and a magnetic stir bar. The vial was placed on a stir plate and stirred vigorously at room temperature. A separate 2 mL half dram vial was charged with $H_2O_2$ (50 wt %, 7.4 µL, 0.12 mmol, 1.2 equiv.) and $CH_3CN$ (0.9 mL). The $H_2O_2$ solution was then added dropwise via syringe to the reaction vial over a period of ca. 45 seconds. The reaction mixture instantly changed from a reddish-purple color to a dark orange. After 15 minutes, an aliquot was taken out and filtered through a $SiO_2$ plug and analyzed by GC. The yields of product 2 for these reactions are listed in the table of FIG. 2, entries 3 and 4. The reactions for entries 1 and 2 of the table of FIG. 2 were performed identically, except that no AcOH was present.

Example 4

Oxidation of cis-4-methylcyclohexyl Pivalate (1) with a Three-Fold Reagent Addition Procedure After approximately 10 minutes, a solution of Fe complex (0.005 mmol, 5 mol %), AcOH (3.0 mg, 0.05 mmol, 50 mol %), in $CH_3CN$ (0.1 mL) was added via pipette to the reaction vials described in the Example 3 (entries 3 and 4). This was followed by $H_2O_2$ (50 wt %, 7.4 µL, 0.12 mmol, 1.2 equiv.) in $CH_3CN$ (0.9 mL) added dropwise over ca. 45 seconds. A third addition was done in the same manner for a total of: Fe complex (15 mol %), AcOH (1.5 equiv.), and $H_2O_2$ (3.6 equiv.). Each addition was allowed to stir for 10 minutes, for a total reaction time of 30 minutes. The isolated yield of product 2 for this reaction with complex 3 was 42%. The yield of product 2 for this reaction with complex 4 is listed in the table of FIG. 2, entry 5. The term "iterative addition protocol" in FIG. 2 means a three-fold reagent addition procedure.

Example 5

Evaluation of Functional Group Compatibility and Substrate Scope in Oxidation of Unactivated $sp^3$ C—H Bonds A 40 mL screwtop vial was charged with the following: complex 4 (23.3 mg, 0.025 mmol, 5 mol %), substrate (0.5 mmol, 1.0 equiv.), $CH_3CN$ (0.75 mL, 0.67 M), and AcOH (15.0 mg, 0.25 mmol, 50 mol %) and a magnetic stir bar. The vial was placed on a stir plate and stirred vigorously at room temperature. A solution of $H_2O_2$ (50 wt %, 36.8 µL, 0.6 mmol, 1.2 equiv.) in $CH_3CN$ (4.5 mL) was added dropwise via syringe over ca. 45-75 seconds. The first drop of peroxide solution instantly changed the reaction mixture from a reddish-purple color to a dark orange, which quickly dissipated back to a bright yellow. As more peroxide was added, this yellow color slowly changed to a darker amber color. Significant decreases in yield were noted when the peroxide solution was added rapidly. No significant difference in yield was noted if the dropwise addition exceeded 75 seconds (up to 150 seconds).

After ca. 10 minutes, a solution of complex 4 (23.3 mg, 0.025 mmol, 5 mol %), AcOH (15 mg, 0.25 mmol, 50 mol %), in $CH_3CN$ (0.5 mL) was added via pipette. This was followed by $H_2O_2$ (50 wt %, 36.8 µL, 0.6 mmol, 1.2 equiv.) in $CH_3CN$ (4.5 mL) added dropwise over ca. 45-75 seconds. A third addition was done in the same manner for a total of: complex 4 (15 mol %), AcOH (1.5 equiv.), and $H_2O_2$ (3.6 equiv.). Each addition was allowed to stir for 10 minutes, for a total reaction time of 30 minutes.

This three-fold reagent addition procedure is noted as "standard conditions" in FIG. 3. In summary, "standard conditions" means that the substrate in $CH_3CN$ (0.67 M), 4 (5 mol %) and AcOH (0.5 equiv.) were combined to form a reaction mixture. To this mixture, $H_2O_2$ (50 wt %, 1.2 equiv.)

in CH₃CN (0.13 M) was added dropwise over ca. 45-75 seconds at room temperature. A second addition of 4 (5 mol %) and AcOH (0.5 equiv.) in CH₃CN (0.05 M) was added, quickly followed by dropwise addition of H₂O₂ (50 wt %, 1.2 equiv.) in CH₃CN (0.13 M). A third addition was done in the same manner for a total of: 4 (15 mol %), AcOH (1.5 equiv.), and H₂O₂ (3.6 equiv.).

For entries 3, 4 and 6-8 in FIG. 3, the products were worked up as follows. The crude mixture was rotovapped down to a minimal amount of CH₃CN. Et₂O was added until a brown precipitate formed. The mixture was filtered through a short plug of celite, concentrated by rotary evaporation and purified by flash chromatography.

For entries 1, 2, 5 and 9 in FIG. 3, the products were worked up as follows. The reaction was quenched with a solution of saturated NaHCO₃. The aqueous layer was extracted with Et₂O (3×30 mL) and the organic layers were combined, dried over MgSO₄, filtered, and concentrated carefully by rotary evaporation at 0° C. to prevent loss of volatile product. The crude product was purified by flash chromatography.

For entry 10 in FIG. 3, the oxidation of cyclohexane to form cyclohexanone (14) was done at 0.1 mmol scale as described in the general procedure of Example 4. Due to volatility, yield of 14 was determined by gas chromatography with response factors using nitrobenzene (40 mol %) as an internal standard. Verification of product was done by comparison with an authentic commercial sample.

Reaction products were characterized by $^1$H NMR, $^{13}$C NMR, and IR. The reaction yields are listed in FIG. 3. The data reported in FIG. 3 is an average of two to three reactions. The specific reaction results are listed below, where the entry number matches the entry number in FIG. 3.

Entry 1: 1-bromo-5-methylhexane (0.5 mmol, 89.6 mg). Purification of 5 by flash chromatography (35% EtOAc/hexanes), run 1 (44.7 mg, 0.229 mmol, 46%), run 2 (45.8 mg, 0.235 mmol, 47%). Average: 47%. Recovered starting material (rSM): 23.3 mg, 0.13 mmol, 26%.

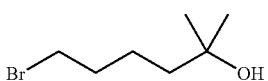

5

Entry 2: 5-methylhexyl acetate (0.5 mmol, 79.1 mg). Purification of 6 by flash chromatography (35% EtOAc/hexanes), run 1 (46.2 mg, 0.265 mmol, 53%), run 2 (46.5 mg, 0.267 mmol, 53%). Average: 53%. Recovered starting material (rSM): 33.9 mg, 0.213 mmol, 43%. HRMS (ESI) m/z calc'd C₉H₁₉O₃ [M+H]⁺: 175.1334, found 175.1333.

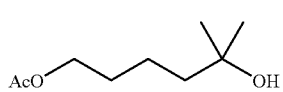

6

Entry 3: methyl 6-methylheptanoate (0.5 mmol, 79.1 mg). Purification of 7 by flash chromatography (35% EtOAc/hexanes), run 1 (51.7 mg, 0.297 mmol, 59%), run 2 (52.7 mg, 0.302 mmol, 60%). Average: 60%. Recovered starting material (rSM): 14.0 mg, 0.088 mmol, 18%. HRMS (ESI) m/z calc'd C₉H₁₈O₃Na [M+Na]⁺: 197.1154, found 197.1160.

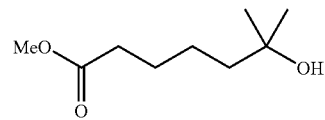

7

Entry 4: 2,2,2-trifluoro-N-(6-methylheptan-2-yl)acetamide (0.5 mmol, 112.6 mg). Purification of 8 by flash chromatography (30% EtOAc/hexanes), run 1 (52.4 mg, 0.217 mmol, 43%), run 2 (51.9 mg, 0.215 mmol, 43%). Average: 43%. Recovered starting material (rSM): 37.2 mg, 0.165 mmol, 33%. HRMS (ESI) m/z calc'd C₁₀H₁₈NO₂F₃Na [M+Na]⁺: 264.1187, found 264.1180.

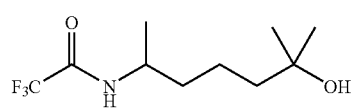

8

Entry 5: 6-methylheptan-2-yl acetate (0.5 mmol, 86.1 mg). Purification of 9 by flash chromatography (25% EtOAc/hexanes), run 1 (49.6 mg, 0.263 mmol, 53%), run 2 (47.2 mg, 0.25 mmol, 50%). Average: 52%. Recovered starting material (rSM): 17.8 mg, 0.10 mmol, 21%. HRMS (ESI) m/z calc'd C₁₀H₂₁O₃ [M+H]⁺: 189.1491, found 189.1493.

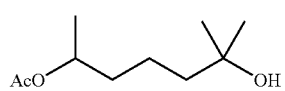

9

Entry 6: (R)-5-((S)-3-methylpentyl)-4,4-dimethyl-1,3-dioxolan-2-one (0.5 mmol, 100.1 mg). Purification of (+)-10 by flash chromatography (40% EtOAc/hexanes), run 1 (60.6 mg, 0.28 mmol, 56%), run 2 (61.8 mg, 0.286 mmol, 57%). Average: 57%. Recovered starting material (rSM): 26.6 mg, 0.133 mmol, 27%. HRMS (ESI) m/z calc'd C₁₁H₂₀O₄Na [M+Na]⁺: 239.1259, found 239.1266. Absolute configuration of entry 6 was determined by comparison with the optical rotation of authentic standard: [α]²³_D +30.80 (c 0.7 CHCl₃). The authentic standard was synthesized via the following route: 1) asymmetric dihydroxylation of commercial (−)-linalool to yield (3R,6R)-2,6-dimethyloct-7-ene-2,3,6-triol; 2) Pd/C hydrogenation of the terminal olefin; 3) carbonate protection of the triol. The optical rotation of (3R,6R)-2,6-dimethyloct-7-ene-2,3,6-triol has an optical rotation of: [α]²³_D +21.7° (c 1.0 CHCl₃). The rotation of this triol is in agreement with the optical rotation reported in the literature of: [α]²⁰_D +25.5° (c 1.0 CHCl₃) (Vidari, G et al. *Tet. Lett.* 1993, 34, 6925).

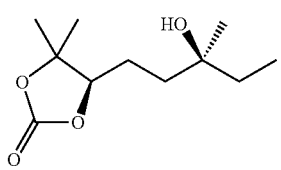

(+)-10

Entry 7: (R)-5-((R)-5,5-dimethyl-2-oxo-1,3-dioxolan-4-yl)-3-methylpentyl acetate (0.5 mmol, 129.2 mg). Purification of (+)-11 by flash chromatography (50% EtOAc/hexanes), run 1 (55.9 mg, 0.204 mmol, 41%), run 2 (60.7 mg, 0.221 mmol, 44%). Average: 43%. Recovered starting material (rSM): 53.6 mg, 0.208 mmol, 42%. HRMS (ESI) m/z calc'd $C_{13}H_{22}O_6Na$ [M+Na]$^+$: 297.1314, found 297.1317. $[\alpha]^{23}_D$+25.4° (c 0.8 CHCl$_3$).

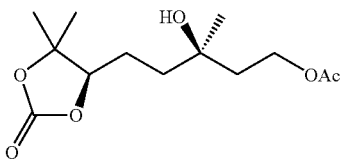

(+)-11

Entry 8: (S)-4-methyl-2-(2,2,2-trifluoroacetamido)pentyl acetate (0.5 mmol, 127.6 mg). Purification of (−)-12 by flash chromatography (50% EtOAc/hexanes). Unoxidized starting material was recycled (collected and re-exposed to another oxidation cycle) one or more times, as noted below. Run 1, recycled 5 times for a total of 91% yield and 8% rSM (recovered starting material): cycle 1 (45.1 mg, 0.167 mmol, 33%), rSM (85.2 mg, 0.335 mmol, 67%); cycle 2 (33.2 mg, 0.122 mmol, 36%), rSM (54.5 mg, 0.214 mmol, 64%); cycle 3 (20.3 mg, 0.075 mmol, 35%), rSM (35.7 mg, 0.140 mmol, 65%); cycle 4 (13.6 mg, 0.050 mmol, 36%), rSM (21.7 mg, 0.085 mmol, 61%); cycle 5 (8.1 mg, 0.030 mmol, 35%), rSM (14.1 mg, 0.059 mmol, 65%); cycle 6: (4.1 mg, 0.015 mmol, 25%), rSM (10.2 mg, 0.040 mmol, 68%). Run 2, recycled 5 times for a total of 89% yield and 8% rSM: cycle 1 (33%, 67% rSM), cycle 2 (36%, 64% rSM), cycle 3 (33%, 67% rSM), cycle 4 (35%, 63% rSM), cycle 5 (28%, 61% rSM), cycle 6 (27%, 72% rSM). Average overall yield: 90%. Average recovered starting material (rSM): 9%. HRMS (ESI) m/z calc'd $C_{10}H_{16}NO_4F_3Na$ [M+Na]$^+$: 294.0929, found 294.0928. $[\alpha]^{23}_D$−30.9° (c 1.0 CHCl$_3$).

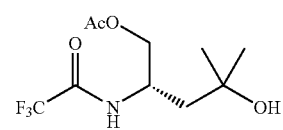

(−)-12

Entry 9: 1-isopropyl-4-methyl-7-oxa-bicyclo[2.2.1]heptane (1,4-cineole) (0.5 mmol, 84.1 mg). Purification of 13 by flash chromatography (10% EtOAc/hexanes), run 1 (45.3 mg, 0.266 mmol, 53%), run 2 (42.7 mg, 0.25 mmol, 50%). Average: 52%. Recovered starting material (rSM): 15.3 mg, 0.2 mmol, 20%. HRMS (ESI) m/z calc'd $C_{10}H_{18}O_2Na$ [M+Na]$^+$: 193.1204, found 193.1207.

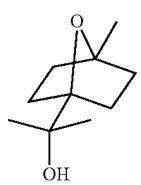

13

Example 6

Substrate Electronic Effects on Site-Selectivity in Hydroxylations of Multiple 3° C—H Bonds The substrates listed in FIG. 4 were oxidized by reaction with complex 4. The oxidation reactions were performed as described in Example 5. For entries 2, 5, 7 and 8 in FIG. 4, the products were worked up as follows. The crude mixture was rotovapped down to a minimal amount of CH$_3$CN. Et$_2$O was added until a brown precipitate formed. The mixture was filtered through a short plug of celite, concentrated by rotary evaporation and purified by flash chromatography.

For entries 1, 3, 4 and 6 in FIG. 4, the products were worked up as follows. The reaction was quenched with a solution of saturated NaHCO$_3$. The aqueous layer was extracted with Et$_2$O (3×30 mL) and the organic layers were combined, dried over MgSO$_4$, filtered, and concentrated carefully by rotary evaporation at 0° C. to prevent loss of volatile product. The crude product was purified by flash chromatography.

Unless otherwise noted, all regioselectivities were determined by GC (without response factors) from the crude reaction mixtures using authentic samples of the proximal oxidation product. For entries 2-4, the proximal oxidation products were isolated from the C—H oxidation reaction separately from the major remote oxidation products. For entries 5-8, authentic samples of proximal oxidation products were synthesized as described below.

Reaction products were characterized by $^1$H NMR, $^{13}$C NMR, and IR. Some products were further characterized by mass spectrometry and/or optical rotation. The reaction yields are listed in FIG. 4. The specific reaction results are listed below, where the entry number matches the entry number in FIG. 4.

Entry 1: 2,6-dimethyloctane (0.5 mmol, 71.1 mg). Purification by flash chromatography (20% Et$_2$O/pentanes) yielded a 1:1 mixture of isomers (remote:proximal) as determined by $^1$H-NMR of the crude reaction mixture using authentic standards made via Pd/C hydrogenation of the commercially available pre-oxidized myrcenol and linalool. The remote isomer was 2,6-dimethyloctan-2-ol (15), and the proximal isomer was 3,7-dimethyloctan-3-ol. The two oxidation regioisomers were inseparable by column chromatography and isolated as a mixture. Run 1 (38.1 mg, 0.241 mmol, 37.9 mg, 0.239 mmol, 48%), run 2 (38.3 mg, 0.242 mmol, 48%). Average: 48%. Recovered starting material (rSM): 20.2 mg, 0.143 mmol, 29%. [Remote:Proximal]=1:1.

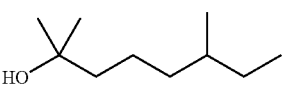

15

Entry 2: (S)-3,7-dimethyloctyl acetate (0.5 mmol, 100.2 mg). Purification by flash chromatography (30% EtOAc/hexanes). The remote product was (S)-7-hydroxy-3,7-dimethyloctyl acetate (16), and the proximal product was (R)-3-hydroxy-3,7-dimethyloctyl acetate. Remote product: run 1 (45.4 mg, 0.210 mmol, 42%), run 2 (46.2 mg, 0.214 mmol, 43%), average: 43%. Regioselectivity was determined by GC using proximal oxidation product isolated from the reaction mixture, and whose characterization data matches previous reports in the literature (Beckwith, A. L. J. et al. *Aust. J. Chem.* 1977, 30, 2177). Recovered starting material (rSM): 34.6 mg, 0.174 mmol, 35%. [Remote:Proximal]=5:1.

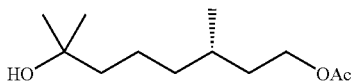

16

Entry 3: (S)-1-bromo-3,7-dimethyloctane (0.5 mmol, 110.6 mg). The remote product was (S)-8-bromo-2,6-dimethyloctan-2-ol (17), and the proximal product was (R)-1-bromo-3,7-dimethyloctan-3-ol. Purification by flash chromatography (10% EtOAc/hexanes), run 1 (45.3, 0.191 mmol, 38%), run 2 (46.4 mg, 0.196 mmol, 39%). Average: 39%. Recovered starting material (rSM): 34.7 mg, 0.158 mmol, 32%. [Remote:Proximal]=9:1.

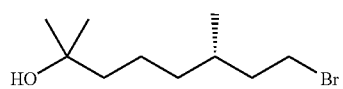

17

Entry 4: (S)-1-fluoro-3,7-dimethyloctane (0.5 mmol, 80.1 mg). The remote product was (S)-8-fluoro-2,6-dimethyloctan-2-ol (18), and the proximal product was (R)-1-fluoro-3,7-dimethyloctan-3-ol. Purification by flash chromatography (10% $Et_2O$/pentanes), run 1 (38.7 mg, 0.22 mmol, 44%), run 2 (37.1 mg, 0.21 mmol, 42%). Average: 43%. Recovered starting material (rSM): 19.6 mg, 0.123 mmol, 20%. [Remote:Proximal]=6:1.

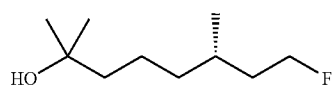

18

Entry 5: 2,6-dimethylheptyl acetate (0.5 mmol, 93.1 mg). The remote product was 6-hydroxy-2,6-dimethylheptyl acetate (19), and the proximal product was 2-hydroxy-2,6-dimethylheptyl acetate. Purification by flash chromatography (25% $Et_2O$/pentanes), run 1 (49.6 mg, 0.245 mmol, 49%), run 2 (48.9 mg, 0.242 mmol, 48%). Average: 49%. Recovered starting material (rSM): 19.8 mg, 0.106 mmol, 21%. [Remote:Proximal]=29:1. Authentic proximal oxidation product was obtained by treating 4-methyl-bromopentane with magnesium turnings and catalytic $I_2$ in $Et_2O$ and reacting with acetoxyacetone. The reaction was quenched with $H_2O$, extracted with $CH_2Cl_2$ and purified by column chromatography (10% EtOAc/hexanes) to yield methyl 2-hydroxy-2,6-dimethylheptyl acetate.

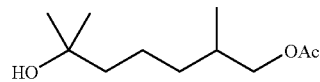

19

Entry 6: 1-bromo-2,6-dimethylheptane (0.5 mmol, 103.6 mg). The remote product was 7-bromo-2,6-dimethylheptan-2-ol (20), and the proximal product was 1-bromo-2,6-dimethylheptan-2-ol. Purification by flash chromatography (10% $Et_2O$/pentanes), run 1 (51.0 mg, 0.229 mmol, 46%), run 2 (54.6 mg, 0.245 mmol, 49%). Average: 48%. Recovered starting material (rSM): 17.8 mg, 0.085 mmol, 17%. [Remote:Proximal]=20:1. Authentic proximal oxidation product was obtained from 2-hydroxy-2,6-dimethylheptyl acetate (entry 5), followed by deprotection ($K_2CO_3$, MeOH, $H_2O$) of the acetate and bromination (AcBr) of the primary alcohol. Upon using this bromination procedure, the secondary alcohol became acetylated, and it was reduced with DIBAL to obtain the proximal oxidation product.

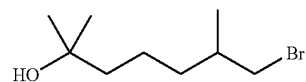

20

Entry 7: 3,7-dimethyloctan-2-one (0.5 mmol, 78.1 mg). The remote product was 7-hydroxy-3,7-dimethyloctan-2-one (21), and the proximal product was 3-hydroxy-3,7-dimethyloctan-2-one. Purification by flash chromatography (35% EtOAc/hexanes), run 1 (46.0 mg, 0.267 mmol, 53%), run 2 (43.1 mg, 0.250 mmol, 50%). Average: 52%. Recovered starting material (rSM): 14.2 mg, 0.183 mmol, 18%. [Remote:Proximal]>99:1. Authentic proximal oxidation product was obtained by treating 1-bromo-4-methylpentane (1 equiv.) with Mg turnings (1 equiv.), followed by 2,3-butandione (1 equiv.) at −78° C. The reaction was quenched $H_2O$, extracted with $CH_2Cl_2$ and purified by column chromatography (15% EtOAc/hexanes) to yield 3-hydroxy-3,7-dimethyloctan-2-one.

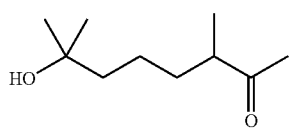

21

Entry 8: methyl 2,6-dimethylheptanoate (0.5 mmol, 86.1 mg). The remote product was methyl 6-hydroxy-2,6-dimethylheptanoate (22), and the proximal product was methyl 2-hydroxy-2,6-dimethylheptanoate. Purification by flash chromatography (35% EtOAc/hexanes), run 1 (53.0 mg, 0.282 mmol, 56%), run 2 (51.0 mg, 0.271 mmol, 54%). Average: 55%. Recovered starting material (rSM): 27.6 mg, 0.161 mmol, 32%. [Remote:Proximal]>99:1. Authentic proximal oxidation product was obtained by treating methyl 2,6-dimethylheptanoate with LDA and MoOPD (Galeyeva, Y. et al. *Synthesis*. 2005, 17, 2875). The reaction was quenched with $H_2O$, extracted with $CH_2Cl_2$ and purified by column chromatography (10% EtOAc/hexanes) to yield methyl 2-hydroxy-2,6-dimethylheptanoate.

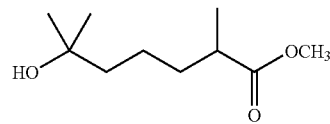

22

Example 7

Substrate Steric Effects on Site-Selectivity in Hydroxylation

Substrate (1R)-(−)-Menthyl acetate (23) (0.5 mmol, 86.1 mg, FIG. 5) was oxidized by reaction with complex 4, using the procedure of Example 5. The crude product mixture was rotovapped down to a minimal amount of $CH_3CN$. $Et_2O$ was added until a brown precipitate formed. The mixture was filtered through a short plug of celite, concentrated by rotary evaporation and purified by flash chromatography (25% EtOAc/hexanes) to isolate (−)-24. Run 1 (52.2 mg, 0.244 mmol, 49%), run 2 (54.5 mg, 0.254 mmol, 51%). Average: 50%. Recovered starting material (rSM): 10.9 mg, 0.055 mmol, 11%. Regioselectivity was determined by 1H-NMR analysis of the crude reaction mixture by comparison of the hydrogen α- to the acetate at 4.99 ppm in (−)-24 and 4.81 ppm in 25 as reported in the literature (Asakawa, Y. et al. *Phytochemistry.* 1988, 27, 3861). The ratio of (−)-24:25 was 11:1.

Example 8

Selective Oxidation at the Most Electron Rich 3° C—H Bond, Followed by In Situ Lactonization Substrate (+)-26 (FIG. 6) was obtained by Jones oxidation and subsequent methylation of the commercial enantioenriched alcohol ((S)-4-methylhexanol, TCI America). This molecule was oxidized by reaction with complex 4 as described in Example 5. The reaction was quenched with a solution of saturated $NaHCO_3$. The aqueous layer was extracted with $Et_2O$ (3×30 mL) and the organic layers were combined, dried over $MgSO_4$, filtered, and concentrated carefully by rotary evaporation at 0° C. to prevent loss of volatile product. The crude product was purified by flash chromatography.

Purification of (+)-27 by flash chromatography (25% EtOAc/hexanes), run 1 (30.8 mg, 0.24 mmol, 48%), run 2 (30.7 mg, 0.24 mmol, 48%). Average: 48%. Recovered starting material (rSM): 16.6 mg, 0.115 mmol, 23%. The experimental data is in agreement with a previous literature report of (+)-27 (Albinati, A. et al. *Perkins Trans. I* 1986, 1405). Enantiomeric excess (ee) was determined by chiral GC analysis J&W cyclodex-β, 45° C. isothermal); major enantiomer $t_R$=12.39 min, minor enantiomer $t_R$=13.29 min; 94% ee. The starting material [(+)-26] is also 94% ee. No erosion in ee was observed.

Purification of (−)-28 by flash chromatography (25% EtOAc/hexanes), run 1 (12.7 mg, 0.080 mmol, 16%), run 2 (13.5 mg, 0.085 mmol, 17%). Average: 17%. This spectroscopic data is in agreement with a previous literature report of this compound (Boers, R. B. et al. *Eur. J. Org. Chem.* 2002, 189).

Example 9

Selective Oxidation at the Least Sterically Hindered, Most Electron Rich Methylene Site Methylation (MeI, $K_2CO_3$) of (+)-32 provided (+)-29. Substrate (+)-29 was oxidized by reaction with complex 4 as described in Example 5. The reaction was quenched with a solution of saturated $NaHCO_3$. The aqueous layer was extracted with $Et_2O$ (3×30 mL) and the organic layers were combined, dried over $MgSO_4$, filtered, and concentrated carefully by rotary evaporation at 0° C. to prevent loss of volatile product. The crude product was purified by flash chromatography.

Purification of (+)-30 by flash chromatography (20% $Et_2O$/pentanes). Part B: run 1 (19.3 mg, 0.136 mmol, 27%), run 2 (19.5 mg, 0.137 mmol, 27%). Average: 27%. This spectroscopic data is in agreement with a previous literature report of this compound (Sugahara, K. et al. *Synthesis,* 1990, 2, 783.).

Purification of (+)-31 by flash chromatography (20% $Et_2O$/pentanes), run 1 (36.5 mg, 0.212 mmol, 42%), run 2 (33.9 mg, 0.197 mmol, 39%). Average: 41%. Recovered starting material (rSM): 11.6 mg, 0.80 mmol, 16%. This spectroscopic data is in agreement with a previous literature report of this compound (Patel, D. V. et al. *J. Am. Chem. Soc.* 1986, 108, 4603.).

Example 10

Selective Oxidation Directed to a Sterically Hindered 3° C—H Site by a Free Carboxylic Acid Carboxylic acid (+)-32 (FIG. 6) was obtained by the asymmetric alkylation as described by Myers (Myers, A. G. et al. *J. Am. Chem. Soc.* 1997, 119, 6496.). Substrate (+)-32 was oxidized by reaction with complex 4 as described in Example 5. The crude mixture was rotovapped down to a minimal amount of $CH_3CN$. $Et_2O$ was added until a brown precipitate formed. The mixture was filtered through a short plug of celite, concentrated by rotary evaporation and purified by flash chromatography.

Purification of (+)-30 by flash chromatography (20% EtOAc/hexanes), run 1 (50.2 mg, 0.353 mmol, 71%), run 2 (50.7 mg, 0.357 mmol, 71%), run 3 (47.6 mg, 0.335 mmol, 67%). Average: 70%. 1H-NMR analysis of the crude mixture revealed no starting material or methyl ketone present upon reaction completion.

Example 11

Oxidation of (+)-artemisinin (+)-Artemisinin (34) (0.5 mmol, 86.1 mg) was oxidized by reaction with complex 4 as described in Example 5, except that only 3.0 mg AcOH (0.5 mmol, 10 mol %) was added to the reaction. Immediately upon completion, the reaction was quenched with a solution of saturated $NaHCO_3$. The aqueous layer was extracted with $Et_2O$ (3×30 mL) and the organic layers were combined, dried over $MgSO_4$, filtered, and concentrated carefully by rotary evaporation at 0° C. to prevent loss of volatile product. The crude product, (+)-10β-hydroxyartemisinin, was purified by flash chromatography. Upon re-isolation of starting material via chromatography, the oxidation was performed again, with identical reagent stoichiometries. The orders of addition were identical, except that complex 4 was added to the substrate.

Purification of (+)-35 by flash chromatography (25% EtOAc/hexanes). Run 1, recycled 2 times (55%): cycle 1 (50.8 mg, 0.170 mmol, 34%), rSM (57.3 mg, 0.202 mmol, 41%); cycle 2 (21.2 mg, 0.071 mmol, 35.0%), rSM (29.2 mg, 0.103 mmol, 51%); cycle 3 (9.7 mg, 0.033 mmol, 31%), rSM (11.4 mg, 0.040 mmol, 39%). Run 2 (53%): cycle 1 (33%, 42% rSM), cycle 2 (31%, 40% rSM), cycle 3 (36%, 31% rSM). Average overall yield: 54%. Average overall recovered starting material (rSM): 8%. This spectroscopic data and optical rotation are in agreement with a previous literature report of this compound (Zhan, J. et al. *Tet Lett.* 2002, 43, 4519.).

Example 12

Attempted Oxidation of α-dihydropicrotoxinin

α-Dihydropicrotoxinin (−)-36 (0.5 mmol, 147.1 mg) was obtained by $PtO_2$ hydrogenation of commercial picrotoxinin (Mercer, D. et al. *J. Chem. Soc.* 1936, 288). This substrate was oxidized by reaction with complex 4 as described in Example 5. Purification by flash chromatography (20% EtOAc/hexanes). Recovered starting material (rSM), run 1 (134.9 mg, 0.458 mmol, 92%), run 2 (135.6 mg, 0.461 mmol, 92%). Average: 92%.

Example 13

Oxidation of 16β-tetrahydrogibberellate Diacetate

16β-tetrahydrogibberellate diacetate (+)-37 was obtained from commercial gibberellic acid via diimide reduction (Cross, B. E. et al. *Perkins Trans. I* 1980, 98) and subsequent peracetylation (Mander, L. N. et al. *Can. J. Chem.* 2004, 82, 293). This substrate was oxidized by reaction with complex 4 as described in Example 5, except that no AcOH was added to the reaction. The reaction was quenched with a solution of saturated $NaHCO_3$. The aqueous layer was extracted with $Et_2O$ (3×30 mL) and the organic layers were combined, dried over $MgSO_4$, filtered, and concentrated carefully by rotary evaporation at 0° C. to prevent loss of volatile product. The crude product was purified by flash chromatography.

Purification of (+)-38 by flash chromatography (30/70/1 EtOAc/hexanes/AcOH). Run 1, recycled once (52%): cycle 1 (41.1 mg, 0.095 mmol, 38%), rSM (43.5 mg, 0.100 mmol, 40%); cycle 2 (15.1 mg, 0.035 mmol, 35%), rSM (14.1 mg, 0.032 mmol, 32%). Run 2 (51%): cycle 1 (36%, 40% rSM), cycle 2 (38%, 22% rSM). Average overall yield: 52%.

Example 14

Oxidation of cis-4-methylcyclohexyl Pivalate (1) with a Continuous Reagent Addition Procedure A 40 mL screwtop vial was charged with the following: cis-4-methylcyclohexyl pivalate (0.5 mmol, 1.0 equiv.), $CH_3CN$ (0.5 mL, 1.0 M), AcOH (3.0 mg, 0.05 mmol, 10 mol %) and a magnetic stir bar. The vial was placed on a stir plate and stirred vigorously at room temperature.

A 5 mL glass syringe was charged with a solution of 4 (69.9 mg, 0.075 mmol, 15 mol %) and AcOH (15.0 mg, 0.25 mmol, 50 mol %) in $CH_3CN$ (3.0 mL), and loaded into a syringe pump. The rate of addition for this syringe pump was set to 0.05 mL/minute.

A 20 mL glass syringe was charged with a solution of $H_2O_2$ (50 wt %, 36.8 μL, 0.6 mmol, 1.2 equiv.) in $CH_3CN$ (15.0 mL) and loaded into a separate syringe pump. The rate of addition for this syringe pump was set to 0.25 mL/minute.

Both syringes had their needles directed into the uncapped reaction vial without touching the sides of the vial. The addition of the mixture containing 4 was started first. After three (3) drops were added to the reaction, the syringe pump containing the oxidant mixture was then started. The two mixtures were added slowly via the syringe pumps over one (1) hour. The reaction was then worked-up and purified as described in Example 3. The yield of purified 2 was 46% (49.5 mg, 0.23 mmol).

The reaction also was performed with twice the amount of oxidant. The oxidant mixture included $H_2O_2$ (50 wt %, 73.6 μL, 1.2 mmol, 2.4 equiv.) in $CH_3CN$ (15.0 mL). The GC yield of purified 2 was 60%, which was the same as the GC yield obtained with complex 4 in Example 4, using the three-fold reagent addition procedure.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:
1. A composition, comprising:
a complex having a structural formula selected from the group consisting of I, its (R,R) enantiomer and mixtures thereof;

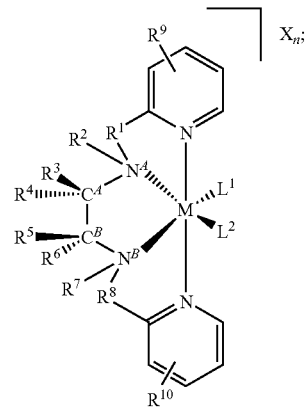

I where M is a metal,
$L^1$ and $L^2$ are ancillary ligands,
X is a counterion,
n is 2 or 3,
$R^1$, $R^2$, $R^7$ and $R^8$ independently are selected from the group consisting of an alkyl group, a heteroalkyl group, an aryl group and a heteroaryl group,
$R^3$, $R^4$, $R^5$ and $R^6$ independently are selected from the group consisting of hydrogen, a halide group, an alkyl group, a heteroalkyl group, an aryl group and a heteroaryl group,
$R^9$ and $R^{10}$ independently are selected from the group consisting of hydrogen, a halide group, an alkyl group, a heteroalkyl group, an aryl group, a heteroaryl group, a nitro group, and a group linking the complex to a surface; and
where $C^A$ and $N^A$, in combination with at least one pair of groups selected from the group consisting of $R^1$ and $R^3$, $R^1$ and $R^4$, $R^2$ and $R^3$, and $R^2$ and $R^4$, form at least one ring.

2. The composition of claim 1, where M is selected from the group consisting of Fe(II), Fe(III), Mn(II) and Mn(III).

3. The composition of claim 1, where $L^1$ and $L^2$ independently are selected from the group consisting of acetone, acetonitrile and a μ-oxo bridge.

4. The composition of claim 1, where $L^1$ and $L^2$ together are a carboxylate group.

5. The composition of claim 1, where X is selected from the group consisting of $Cl^-$, $Br^-$, $AcO^-$, $TfO^-$, $CF_3CO_2^-$, $BF_4^-$, $ClO_4^-$, $ReO_4^-$, $AsF_6^-$, and $SbF_6^-$.

6. The composition of claim 1, where
$R^1$, $R^2$, $R^7$ and $R^8$ independently are an alkyl group, and
$R^3$, $R^4$, $R^5$ and $R^6$ independently are selected from the group consisting of hydrogen and an alkyl group.

7. The composition of claim 1, where $C^B$ and $N^B$, together with at least one pair of groups selected from the group consisting of $R^8$ and $R^6$, $R^8$ and $R^5$, $R^7$ and $R^6$, and $R^7$ and $R^5$, form at least one ring.

8. The composition of claim 1, where $C^A$ and $C^B$, together with at least one pair of groups selected from the group consisting of $R^3$ and $R^5$, $R^4$ and $R^6$, $R^4$ and $R^5$, and $R^3$ and $R^6$, form at least one ring.

9. A composition, comprising:

a complex having a structural formula selected from the group consisting of II, its (R,R) enantiomer and mixtures thereof;

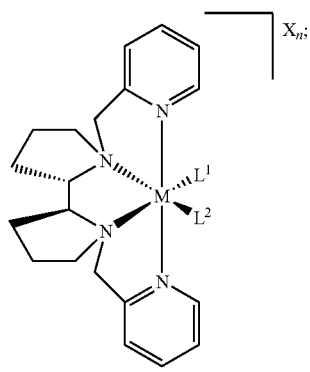

II where M is a metal selected from the group consisting of Fe(II), Fe(III), Mn(II) and Mn(III), $L^1$ and $L^2$ are ancillary ligands, where $L^1$ and $L^2$ independently are selected from the group consisting of acetone, acetonitrile and a μ-oxo bridge; or $L^1$ and $L^2$ together are a carboxylate group, X is a counterion selected from the group consisting of $Cl^-$, $Br^-$, $AcO^-$, $TfO^-$, $CF_3CO_2^-$, $BF_4^-$, $ClO_4^-$, $ReO_4^-$, $AsF_6^-$, and $SbF_6^-$, and n is 2 or 3.

10. The composition of claim 9, where M is Fe(II).

11. The composition of claim 9, where $L^1$ and $L^2$ are acetonitrile.

12. The composition of claim 9, where X is $SbF_6^{31}$.

13. The composition of claim 9, where
M is Fe(II),
$L^1$ and $L^2$ are acetonitrile,
X is $SbF_6^{31}$, and
n is 2.

14. A method of selectively oxidizing an sp3-hybridized C—H bond in a molecule, comprising:
reacting the molecule and an oxidant in a first reaction mixture comprising the composition of claim 1, and
providing an oxidized product in the first reaction mixture.

15. The method of claim 14, where the oxidant is selected from the group consisting of hydrogen peroxide, ozone, a peracid, an alkyl hydroperoxide, or a periodinane.

16. The method of claim 14, where the first reaction mixture further comprises a solvent comprising acetonitrile.

17. The method of claim 14, where the first reaction mixture further comprises an alkyl carboxylic acid.

18. A method of selectively oxidizing an sp3-hybridized C—H bond in a molecule, comprising:
reacting the molecule and an oxidant in a first reaction mixture comprising the composition of claim 9, and
providing an oxidized product in the first reaction mixture.

19. A method of modeling the interaction of a cytochrome P-450 enzyme with a molecule that includes at least one $sp^3$-hybridized C—H bond, comprising:
reacting the molecule and an oxidant in a reaction mixture comprising the composition of claim 1,
providing at least one oxidized product in the reaction mixture; and
analyzing the at least one oxidized product.

* * * * *